(12) United States Patent
Rao et al.

(10) Patent No.: US 8,445,687 B2
(45) Date of Patent: May 21, 2013

(54) PROCESS FOR THE PREPARATION OF A RAF KINASE INHIBITOR AND INTERMEDIATES FOR USE IN THE PROCESS

(75) Inventors: Dharmaraj Ramachandra Rao, Maharashtra (IN); Rajendra Narayanrao Kankan, Maharashtra (IN); Maruti Ghagare, Maharashtra (IN); Sandip Chikhalikar, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 12/677,195

(22) PCT Filed: Sep. 10, 2008

(86) PCT No.: PCT/GB2008/003048
§ 371 (c)(1),
(2), (4) Date: Jul. 23, 2010

(87) PCT Pub. No.: WO2009/034308
PCT Pub. Date: Mar. 19, 2009

(65) Prior Publication Data
US 2010/0311980 A1    Dec. 9, 2010

(30) Foreign Application Priority Data

Sep. 10, 2007  (IN) .................. 1733/MUM/2007
Sep. 10, 2007  (IN) .................. 1734/MUM/2007

(51) Int. Cl.
*C07D 213/81*   (2006.01)
*A61K 31/44*    (2006.01)

(52) U.S. Cl.
USPC ............................. 546/298; 514/350

(58) Field of Classification Search
None
See application file for complete search history.

(56) References Cited

U.S. PATENT DOCUMENTS 3,407,056 A  10/1968  Schwartz
6,242,385 B1  6/2001  Weiland et al.

FOREIGN PATENT DOCUMENTS

| CH | 497117 | 6/1970 |
|---|---|---|
| EP | 1659121 A1 | 5/2006 |
| EP | 1939205 A1 | 7/2008 |
| FR | 1484461 | 6/1967 |
| WO | 0041698 A1 | 7/2000 |
| WO | 0042012 A1 | 7/2000 |
| WO | 2005121147 A1 | 12/2005 |
| WO | 2006034796 A1 | 4/2006 |
| WO | 2007064931 A2 | 6/2007 |
| WO | 2009034308 A2 | 3/2009 |
| WO | 2009034308 A3 | 3/2009 |

OTHER PUBLICATIONS

Foreign communication from the priority application—International Preliminary Report on Patentability, PCT/GB2008/003048, Feb. 17, 2010, 20 pages.
Foreign communication from the priority application—International Search Report and Written Opinion, PCT/GB2008/003048, May 26, 2009, 17 pages.
Vauthey, Isabelle, et al., "An environmentally benign access to carbamates and ureas," Tetrahedron Letters, 2000, vol. 41, pp. 6347-6350, XP-002516850, Pergamon Press, Elsevier Science Ltd.

*Primary Examiner* — D M Seaman
*Assistant Examiner* — Heidi Reese
(74) *Attorney, Agent, or Firm* — Conley Rose, P.C.; Rodney B. Carroll

(57) ABSTRACT

There is provided a process for preparing sorafenib or a salt thereof comprising the use of a compound of formula (A)

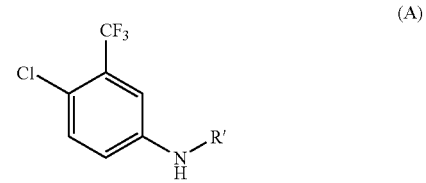

(A)

wherein R' is selected from the group consisting of hydrogen, —C(O)OA, —C(O)CX$_3$, —C(O)NH$_2$, —C(O)—NHOH or

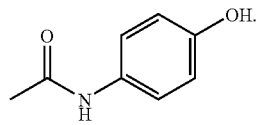

There is also provided intermediate compounds of general formula (A), N-methyl-4-(4-ureidophenoxy)picolinamide, 4-(2-(methylcarbamoyl)pyridin-4-yloxy)phenylcarbamate derivative and N-methyl-4-(4-(2,2,2-trihaloacetamido)phenoxy)picolinamide, processes for their preparation and their use in the preparation of sorafenib.

16 Claims, No Drawings

PROCESS FOR THE PREPARATION OF A RAF KINASE INHIBITOR AND INTERMEDIATES FOR USE IN THE PROCESS

CROSS-REFERENCE TO RELATED APPLICATIONS

This application is a filing under 35 U.S.C. 371 of International Application No. PCT/GB2008/003048 filed Sep. 10, 2008, entitled "Process for the Preparation of a RAF Kinase Inhibitor and Intermediates for Use in the Process," claiming priority of Indian Patent Application Nos. 1734/MUM/2007 and 1733/MUM/2007, both filed Sep. 10, 2007, which applications are incorporated by reference herein in their entirety.

TECHNICAL FIELD OF THE INVENTION

The present invention relates to a novel process for the preparation of 4-(4-{3-[4-chloro-3-(trifluoromethyl)phenyl]ureido}phenoxy)-$N^2$-methylpyridine-2-carboxamide or its pharmaceutically acceptable salts.

BACKGROUND OF THE INVENTION 4-(4-{3-[4-chloro-3-(trifluoromethyl)phenyl]ureido}phenoxy)-$N^2$-methylpyridine-2-carboxamide is commonly known as sorafenib (I). Sorafenib is prepared as its tosylate salt. Sorafenib blocks the enzyme RAF kinase, a critical component of the RAF/MEK/ERK signaling pathway that controls cell division and proliferation; in addition, sorafenib inhibits the VEGFR-2/PDGFR-beta signaling cascade, thereby blocking tumor angiogenesis.

Sorafenib, marketed as Nexavar™ by Bayer, is a drug approved for the treatment of advanced renal cell carcinoma (primary kidney cancer). It has also received "Fast Track" designation by the FDA for the treatment of advanced hepatocellular carcinoma (primary liver cancer). It is a small molecular inhibitor of RAF kinase, PDGF (platelet-derived growth factor), VEGF receptor 2 and 3 kinases and c Kit the receptor for stem cell factor.

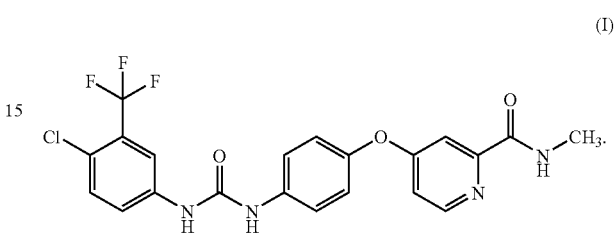

(I)

Sorafenib and pharmaceutically acceptable salts thereof is disclosed in WO0042012. Sorafenib is also disclosed in WO0041698. Both these patents disclose processes for the preparation of sorafenib.

WO0042012 and WO0041698 describe the process as given in Scheme I which comprises reacting picolinic acid (II) with thionyl chloride in dimethyl formamide (DMF) to form acid chloride salt (III). This salt is then reacted with methylamine dissolved in tetrahydrofuran (THF) to give carboxamide (IV). This carboxamide when further reacted with 4-aminophenol in anhydrous DMF and potassium tert-butoxide 4-(2-(N-methylcarbamoyl)-4-pyridyloxy)aniline (V) is formed. Subsequent reaction of this aniline with 4-chloro-3-(trifluoromethyl)phenyl isocyanate (VI) in methylene chloride yields sorafenib (I). The reaction is represented by Scheme I as given below.

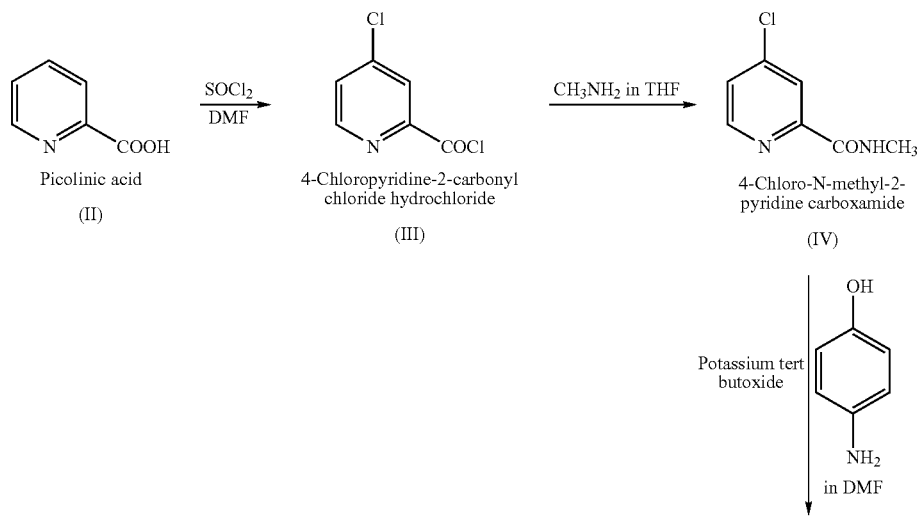

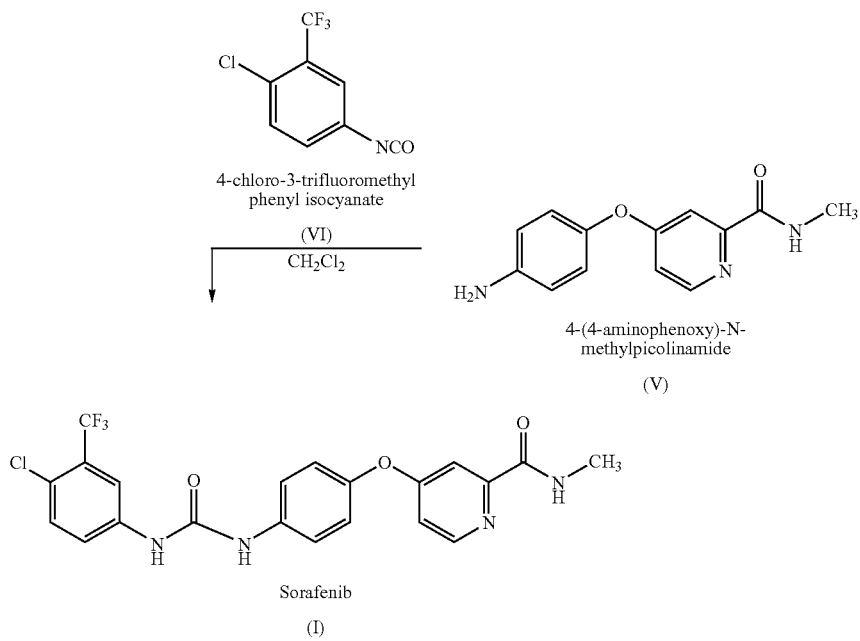

WO2006034796 also discloses a process for the preparation of sorafenib and its tosylate salt. The process comprises reacting 2-picolinic acid (II) with thionyl chloride in a solvent inert toward thionyl chloride without using dimethyl formamide to form acid chloride salt (III). This acid salt on further reaction with aqueous solution methylamine or gaseous methylamine gives compound (IV). Compound (IV) is then reacted with 4-aminophenol with addition of a carbonate salt in the presence of a base to yield compound (V).

Compound (V) can also be obtained by reacting compound (IV) with 4-aminophenol in the presence of water with addition of a phase transfer catalyst. Compound (V) when reacted with 4-chloro-3-(trifluoromethyl)phenyl isocyanate (VI) in a non-chlorinated organic solvent, inert towards isocyanate gives sorafenib (I). Sorafenib by admixing with p-toluenesulfonic acid in a polar solvent gives sorafenib tosylate (VII). The reaction is represented by Scheme II as given below.

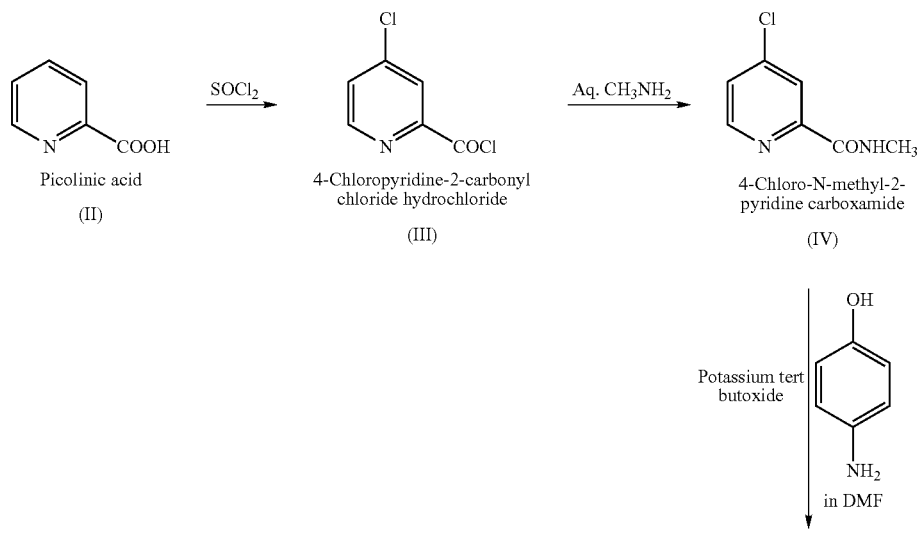

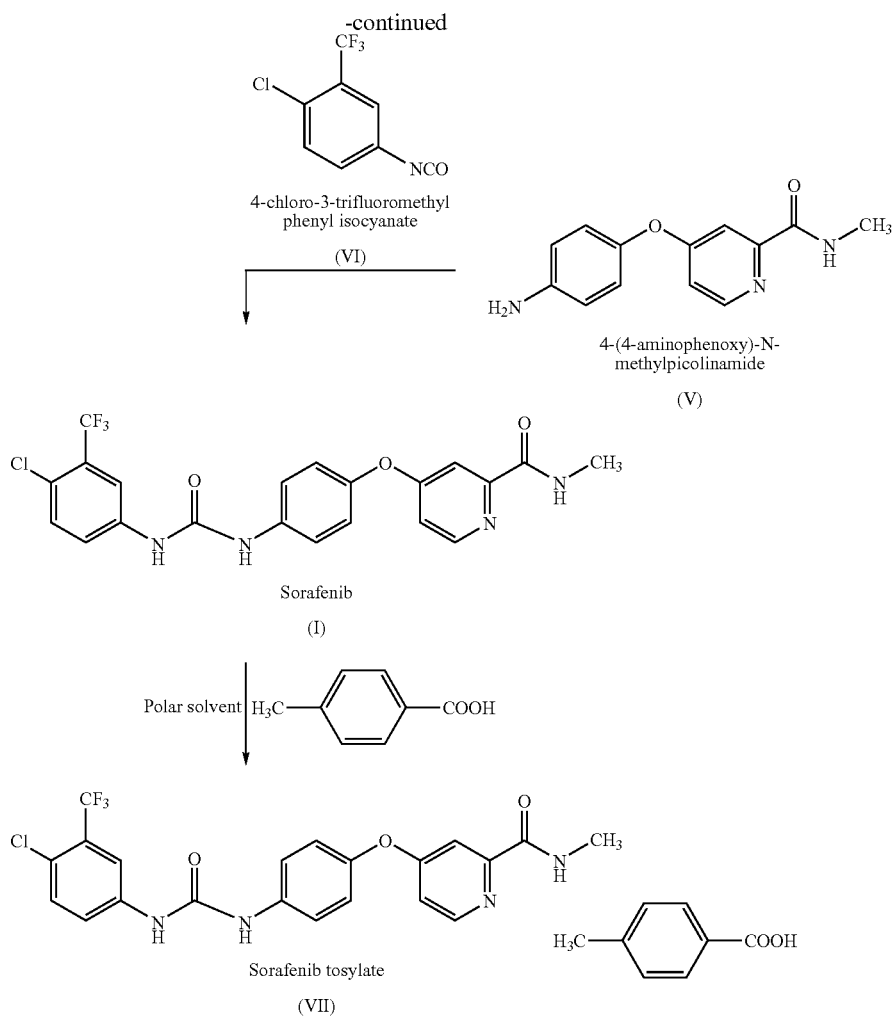

A key step in the synthesis of sorafenib is the formation of the urea bond. The processes disclosed in the prior art involve reactions of an isocyanate with an amine. These isocyanate compounds though commercially available are very expensive. Further synthesis of isocyanate is very difficult which requires careful and skillful handling of reagents.

Isocyanate is prepared by reaction of an amine with phosgene or a phosgene equivalent, such as bis(trichloromethyl) carbonate (triphosgene) or trichloromethyl chloroformate (diphosgene). Isocyanate can also be prepared by using a hazardous reagent such as an azide. Also, the process for preparation of an isocyanate requires harsh reaction conditions such as strong acid, higher temperature, etc. Further, this isocyanate is reacted with an amine to give urea.

Reactions of isocyanates suffer from one or more disadvantages. For example, phosgene or phosgene equivalents are hazardous and dangerous to use and handle on a large scale. These reagents are also not environmentally friendly. Isocyanates themselves are thermally unstable compounds and undergo decomposition on storage and they are incompatible with a number of organic compounds. Thus, the use of isocyanate is not well suited for industrial scale application.

Hence, there is a need to develop simple and less hazardous process for large scale production. There is also a need to avoid, as far as possible, the use of hazardous chemicals and a need to use safer reagents which can be stored, handled without special precaution, and which are environmentally friendly.

OBJECTS OF THE INVENTION

It is an object of the present invention to provide novel key intermediates for the synthesis of sorafenib or its pharmaceutically acceptable salts.

It is another object of the present invention to provide processes for the preparation of the novel key intermediates useful in the synthesis of sorafenib or its pharmaceutically acceptable salts.

It is yet another object of this invention to provide simple and novel processes for the preparation of sorafenib or its pharmaceutically acceptable salts using the novel key intermediates.

SUMMARY OF THE INVENTION

According to a first aspect of the present invention, there is provided a compound of formula (A)

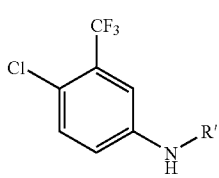
(A)

wherein R' is selected from the group consisting of —C(O)OA, —C(O)CX$_3$, —C(O)NH$_2$, —C(O)—NHOH or

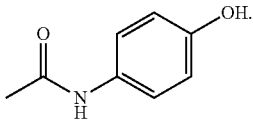

These novel compounds of formula (A) may be used in a number of novel processes for preparing sorafenib or a salt thereof. None of the processes for preparing the compounds of formula (A), nor any of the processes for preparing sorafenib or a salt thereof using the compounds of formula (A), involve the use of isocyanate derivatives. As discussed above, isocyanates are highly disadvantageous because they are expensive, hazardous to make, and hazardous to use. The compounds of formula (A) of the present invention on the other hand, are simple and safe to use so are much more suitable for industrial scale-up compared to the isocyanates of the prior art. Therefore, the processes of the present invention are highly advantageous.

In an embodiment, R' in compound (A) is hydrogen, and the compound of formula (A) is 4-chloro-3-trifluoromethylaniline. In this embodiment, the compounds that are condensed with 4-chloro-3-trifluoromethylaniline to form sorafenib (compounds (6) and (7), described in more detail below) are novel. These intermediates are highly advantageous for the same reasons as given above, i.e., they are safe and simple to use compared to isocyanates used in the prior art.

In another embodiment, R' is

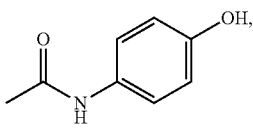

and the compound of formula (A) is compound (1) described in more detail below.

In another embodiment, R' is —C(O)OA, and the compound of formula (A) is carbamate derivative (2) described in more detail below.

In another embodiment, R' is —C(O)CX$_3$, and the compound of formula (A) is anilide derivative (3) described in more detail below.

In another embodiment, R' is —C(O)NH$_2$, and the compound of formula (A) is urea derivative (4) described in more detail below.

In another embodiment, R' is —C(O)—NHOH, and the compound of formula (A) is hydroxy urea derivative (9) described in more detail below.

According to another aspect of the present invention, there is provided a process for preparing sorafenib or a salt thereof comprising the use of a compound of formula (A)

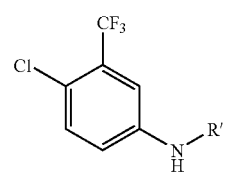
(A)

wherein R' is selected from the group consisting of hydrogen, —C(O)OA, —C(O)CX$_3$, —C(O)NH$_2$, —C(O)—NHOH or

According to another aspect of the present invention, there is provided a compound of formula (1)

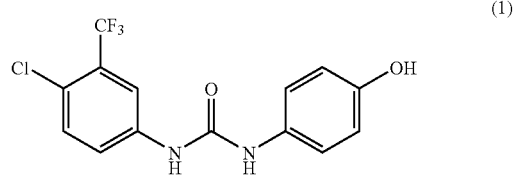 [SMILES: O=C(Nc1ccc(O)cc1)Nc1ccc(Cl)c(C(F)(F)F)c1]
(1)

According to another aspect of the present invention, there is provided a process for preparing a compound of formula (1) comprising reacting carbamate derivative (2)

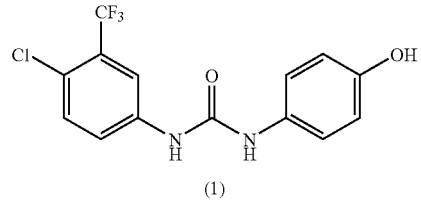

Carbamate derivative
(2)

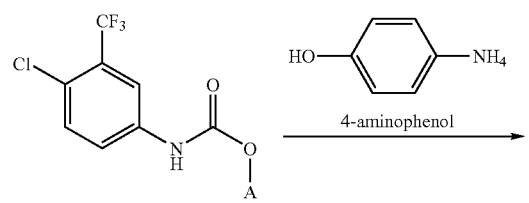
(1)

wherein A is alkyl or aryl, with 4-aminophenol in the presence of a solvent to obtain carbamate derivative (2). In an embodiment, alkyl is C$_{1-3}$ alkyl, suitably methyl, ethyl, isopropyl or n-propyl. In another embodiment, aryl is phenyl. In an embodiment, the carbamate derivative may be prepared by the process described below.

The reaction of carbamate derivative (2) with 4-aminophenol may be carried out at a temperature ranging from 0 to 60° C., preferably from 40 to 60° C.

The solvent may be an include organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile or mixtures thereof.

According to another aspect of the present invention, there is provided a process for preparing a carbamate derivative (2) comprising reacting 3-trifluoromethyl-4-chloroaniline with a haloformate (2a) or a carbonate derivative (2b)

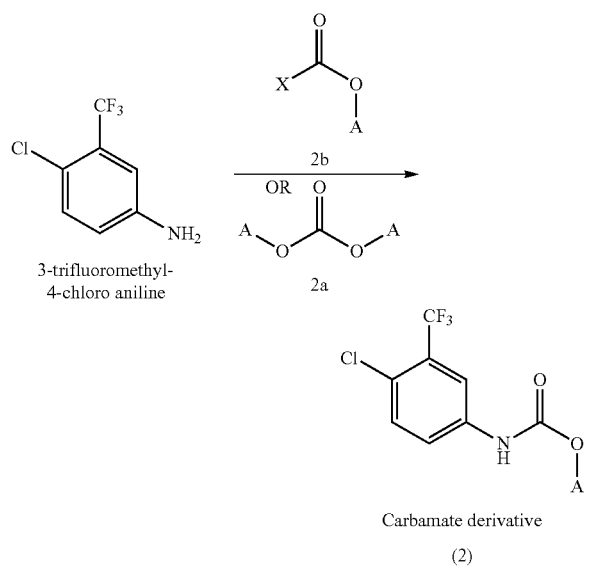

wherein in haloformate (2a), A is alkyl or aryl, and in carbonate (2b), A is alkyl, aryl or the two A groups taken together form a 5 to 7 membered ring, in the presence of a base and a solvent to obtain carbamate derivative (2). The carbamate derivative (2) may be used in the process described above for preparing the compound of formula (1).

In an embodiment, alkyl is $C_{1-3}$ alkyl, suitably methyl, ethyl, iso-propyl or n-propyl. In another embodiment, aryl is phenyl. The carbonate derivative may be an aliphatic compound. Alternatively, the carbonate derivative may be a cyclic compound, i.e., the two A groups may be joined to form a 5 to 7 membered ring. The ring members making up the A group are suitably $CH_2$ groups. In an embodiment, the moiety of the carbonate joining the two oxygen ring members is —$CH_2CH_2$—. In an embodiment, the haloformate or carbonate derivatives are selected from but not limited to phenyl chloroformate, methyl chloroformate, ethyl chloroformate, diethyl carbonate and [1,3]dioxolan-2-one.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine and 1,8-diazabicyclo [5.4.0]undec-7-ene.

The reaction of 3-trifluoromethyl-4-chloroaniline with the haloformate or carbonate derivative may be carried out at a temperature ranging from −10 to 25° C., preferably from −5 to 5° C. Typically, the haloformate or carbonate derivative is added slowly so as to maintain the desired temperature of the reaction mass during the addition of the haloformate or carbonate derivative.

According to another aspect of the present invention, there is provided a process for preparing a compound of formula (1) comprising reacting anilide derivative (3) with 4-aminophenol

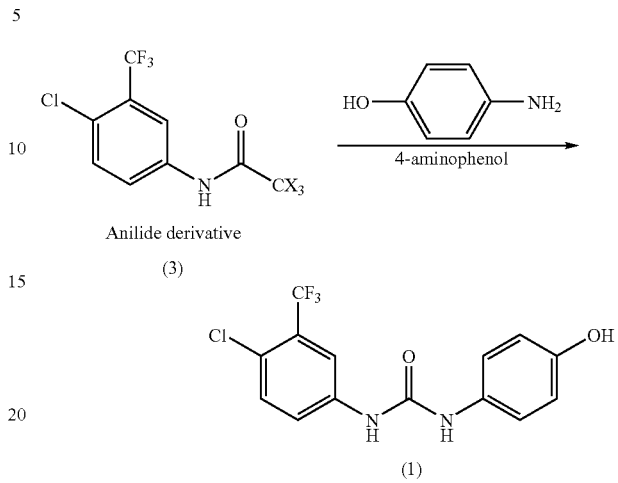

wherein X is halogen, in a solvent to obtain compound (1). In an embodiment, the compound of formula (3) is prepared according to the process described below.

In an embodiment, the reaction is carried out at a temperature ranging from 100 to 140° C., preferably from 110 to 120° C.

The solvent may include organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

According to another aspect of the present invention, there is provided a process for preparing anilide derivative (3) comprising reacting 3-trifluoromethyl-4-chloroaniline with a trihaloalkyl halide, a trihaloalkyl anhydride, or a trihaloalkyl ester,

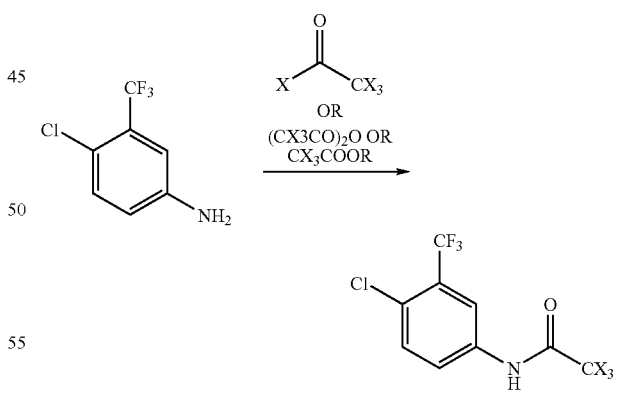

wherein X is halogen and R is alkyl, to obtain anilide derivative (3).

X in trihaloalkyl halide or anhydride or ester is halogen such as chlorine, bromine or iodine, preferably chlorine.

In an embodiment, the trihaloalkyl halide or anhydride or ester is selected from trichloroacetyl chloride, tribromoacetyl chloride, trichloro acid anhydride, ethyl trichloroacetate, methyl trichloroacetate, phenyl trichloroacetate, and ethyl tribromoacetate.

The reaction of the trihaloalkyl halide or anhydride or ester may be carried out at a temperature ranging from −5 to 25° C. Typically, the trihaloalkyl halide or anhydride or ester is added slowly so as to maintain the desired temperature of the reaction mass during the addition the trihaloalkyl halide or anhydride or ester.

Optionally, the reaction is carried out in the presence of a base. The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine and 1,8-diazabicyclo [5.4.0]undec-7-ene.

According to another aspect of the present invention, there is provided a process for preparing a compound of formula (1) comprising reacting urea derivative (4) with 4-aminophenol in a solvent to obtain compound (1).

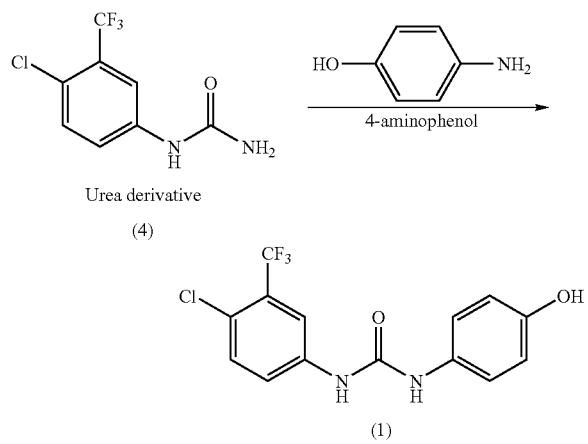

In an embodiment, the urea derivative (4) is prepared according to the process described below.

In an embodiment, the urea derivative (4) is mixed with 4-aminophenol and the reaction mass is heated to a temperature ranging from 70 to 100° C., preferably from 80 to 90° C.

The solvent may be an organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

According to another aspect of the present invention, there is provided a process for preparing urea derivative (4) comprising reacting 3-trifluoromethyl-4-chloroaniline with an alkali cyanate in the presence of an acid to obtain urea derivative (4)

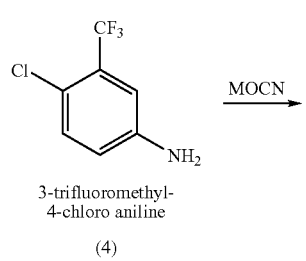

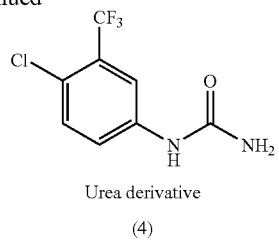

wherein M is an alkali metal. In an embodiment, the urea derivative (4) may be used in the process described above for preparing the compound of formula (1).

M in the alkali cyanate is an alkali metal such as sodium, potassium, calcium or lithium, preferably sodium. The alkali cyanate is typically added slowly to 3-trifluoromethyl-4-chloroaniline suitably at a temperature ranging from 40 to 50° C.

The acid may be an organic or inorganic acid. The organic acid may be selected from acids such as but not limited to acetic acid, oxalic acid, benzoic acid, citric acid, succinic acid, benzene sulphonic acid, tartaric acid, or methane sulphonic acid. The inorganic acid may be selected from acids such as but not limited to hydrochloric acid, hydrobromic acid, sulphuric acid, nitric acid, or phosphoric acid.

According to another aspect of the present invention, there is provided a process for preparing a compound of formula (1) comprising reacting phenoxy urea (5) with 3-trifluoromethyl-4-chloroaniline in a solvent in the presence of a base to obtain compound (1).

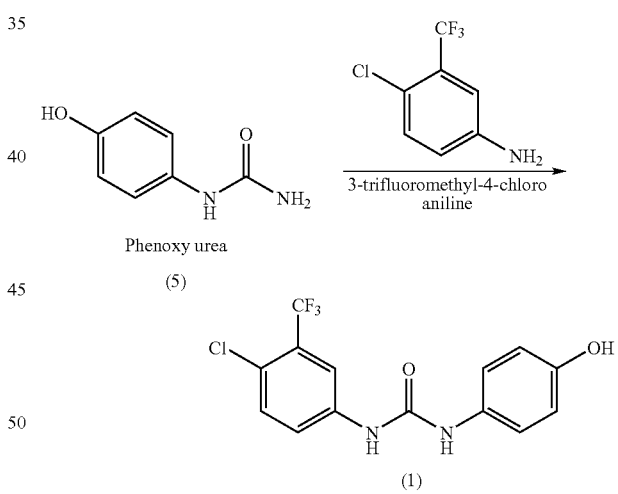

In an embodiment, the phenoxy urea (5) is prepared according to the process described below.

In an embodiment, the reaction of the phenoxy urea (5) and 3-trifluoromethyl-4-chloroaniline is carried out at a temperature ranging from 100 to 150° C.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine and 1,8-diazabicyclo [5.4.0]undec-7-ene.

The solvent may be an organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

According to another aspect of the present invention, there is provided a process for preparing phenoxy urea (5) comprising reacting 4-aminophenol

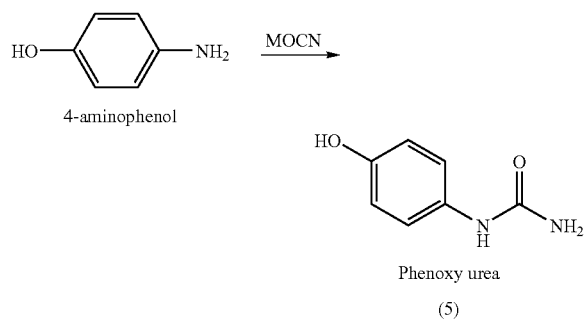

wherein M is an alkali metal, with an alkali cyanate in the presence of an acid to obtain phenoxy urea (5). In an embodiment, the phenoxy urea (5) is used in a process described above for preparing the compound of formula (1).

M in the alkali cyanate is an alkali metal such as sodium, potassium, calcium or lithium, preferably sodium.

The acid may be an organic or inorganic acid. The organic acid may be selected from acids such as but not limited to acetic acid, oxalic acid, benzoic acid, citric acid, succinic acid, benzene sulphonic acid, tartaric acid, or methane sulphonic acid. The inorganic acid may be selected from acids such as, but not limited to, hydrochloric acid, hydrobromic acid, sulphuric acid, nitric acid, or phosphoric acid.

The alkali cyanate is typically added slowly to the 4-aminophenol. The reaction may be carried out at a temperature ranging from 20 to 25° C.

According to another aspect of the present invention, there is provided a process for preparing sorafenib or a salt thereof comprising reacting a compound of formula (1) with 4-chloro-N-methyl-2-pyridine carboxamide in the presence of a base to obtain sorafenib and optionally converting sorafenib to a salt thereof.

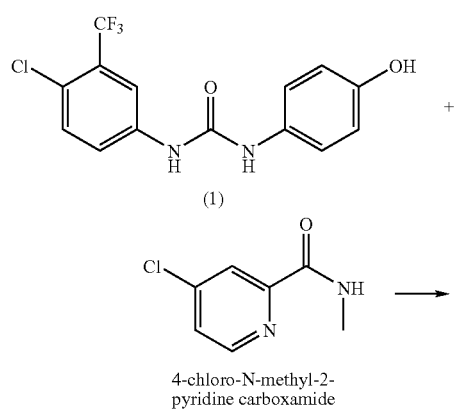

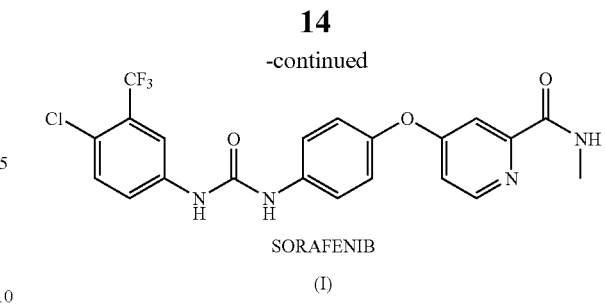

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine and 1,8-diazabicyclo[5.4.0]undec-7-ene.

The reaction may be carried out at temperature a ranging from 20 to 80° C.

In an embodiment, sorafenib is converted to sorafenib tosylate.

In an embodiment, the compound of formula (1) has been prepared according to any one of the processes described above.

According to another aspect of the present invention, there is provided a compound of formula (6).

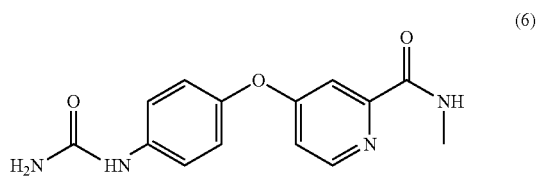 [SMILES: CNC(=O)c1cc(Oc2ccc(NC(N)=O)cc2)ccn1]

According to another aspect of the present invention, there is provided a process for preparing a compound of formula (6) comprising reacting 4-(4-aminophenoxy)-N-methylpicolinamide or a salt thereof

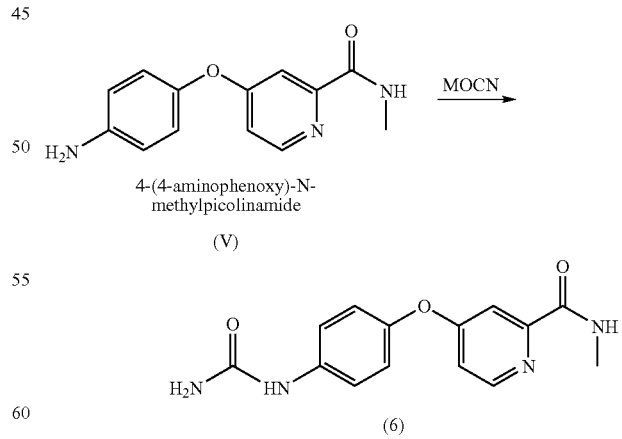

wherein M is an alkali metal, with an alkali cyanate in the presence of a protic solvent to obtain compound (6). In an embodiment, the compound of formula (6) is used in the process described above for preparing sorafenib or a salt thereof.

M in the alkali cyanate is an alkali metal such as sodium, potassium, calcium or lithium, preferably sodium.

The protic solvent may be selected from acids such as, but not limited to, acetic acid, oxalic acid, benzoic acid, citric acid, succinic acid, benzene sulphonic acid, tartaric acid, methane sulphonic acid, or an inorganic acid. The inorganic acid may be selected from acids such as, but not limited to, hydrochloric acid, hydrobromic acid, sulphuric acid, nitric acid, or phosphoric acid.

The alkali cyanate may be added to 4-(4-aminophenoxy)-N-methylpicolinamide or its salt at 20-25° C. The addition of alkali cyanate to 4-(4-aminophenoxy)-N-methylpicolinamide is typically carried out slowly so as to maintain the desired temperature of the reaction mass during the addition of the alkali metal cyanate. After addition, the reaction mass may be stirred to obtain intermediate (6).

According to another aspect of the present invention, there is provided a process for preparing sorafenib or a salt thereof comprising reacting compound (6) with 4-chloro-3-trifluoromethylaniline in the presence of a base and a solvent to obtain sorafenib and optionally converting sorafenib to a salt thereof.

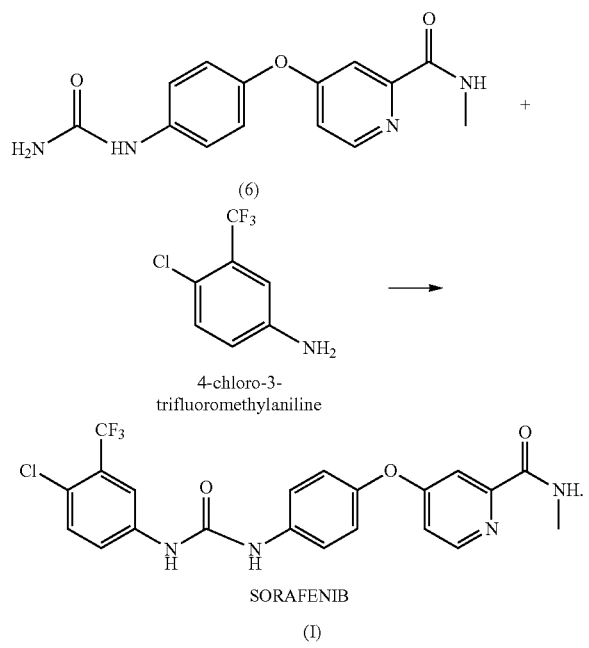

In an embodiment, the base is potassium tertbutoxide, potassium hydroxide, sodium hydroxide, ammonium hydroxide, sodium methoxide, potassium methoxide, potassium carbonate, sodium carbonate, pyridine, dimethyl amine, triethylamine, N,N-diisopropylethyl amine or 1,8-diazabicyclo[5.4.0]undec-7-ene.

The solvent may include organic solvent such as water, methylene dichloride (MDC), ethylene dichloride, tetrahydrofuan (THF), 1,4-dioxane, methylisobutyl ketone, ethylmethyl ketone, toluene, N,N-dimethylformamide (DMF), dimethylsulfoxide (DMSO), ethyl acetate, acetone, acetonitrile, or mixtures thereof.

In an embodiment, sorafenib is converted to sorafenib tosylate.

In an embodiment, the compound of formula (6) has been prepared according to a process described above.

According to another aspect of the present invention, there is provided a compound of formula (7)

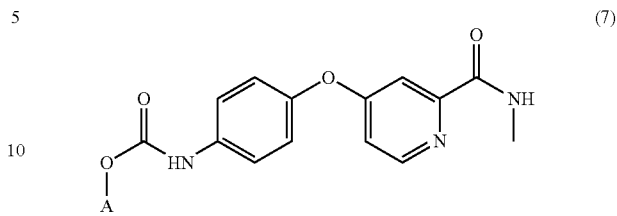

wherein A is alkyl or aryl. In an embodiment, alkyl is $C_{1-3}$ alkyl, suitably methyl, ethyl, iso-propyl or n-propyl. In another embodiment, aryl is phenyl.

According to another aspect of the present invention, there is provided a process for preparing the compound of formula (7) comprising reacting 4-(4-aminophenoxy)-N-methylpicolinamide or a salt thereof with a haloformate (2a) or a carbonate derivative (2b)

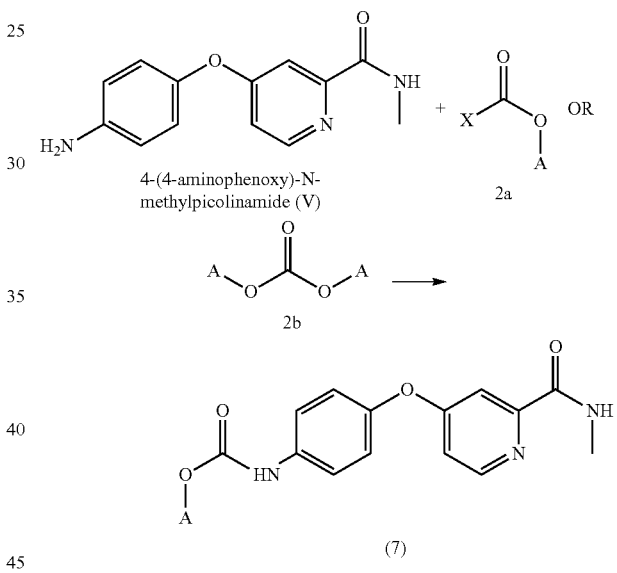

wherein in haloformate (2a), A is alkyl or aryl, and in carbonate (2b), A is alkyl, aryl, or the two A groups taken together form a 5 to 7 membered ring, in the presence of a base to obtain the compound of formula (7).

In an embodiment, the 4-(4-aminophenoxy)-N-methylpicolinamide or a salt thereof is reacted with the haloformate or a carbonate derivative at a temperature ranging from −5 to 25° C. preferably from 0 to 5° C.

In an embodiment, alkyl is $C_{1-3}$ alkyl, suitably methyl, ethyl, iso-propyl or n-propyl. In another embodiment, aryl is phenyl. The carbonate derivative may be an aliphatic compound. Alternatively, the carbonate derivative may be a cyclic compound, i.e., the two A groups may be joined to form a ring. In an embodiment, the moiety of the carbonate joining the two oxygen ring members is —$CH_2CH_2$—. In an embodiment, the haloformate or carbonate derivatives are selected from, but not limited to, phenyl chloroformate, methyl chloroformate, ethyl chloroformate, diethyl carbonate, and [1,3] dioxolan-2-one.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine, and 1,8-diazabicyclo [5.4 0]undec-7-ene.

According to another aspect of the present invention, there is provided a process for preparing sorafenib or a salt thereof comprising reacting compound (7) with 4-chloro-3-trifluoromethylaniline

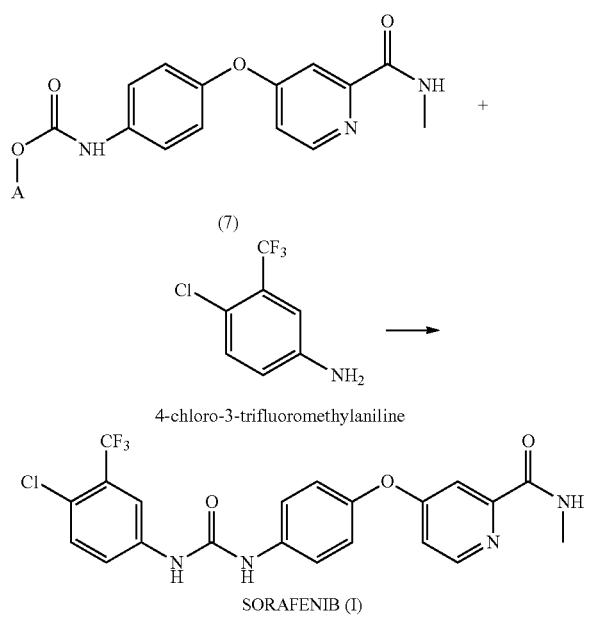

wherein A is alkyl or aryl, to obtain sorafenib and optionally converting the sorafenib to a salt thereof. In an embodiment, alkyl is $C_{1-3}$ alkyl, suitably methyl, ethyl, iso-propyl or n-propyl. In another embodiment, aryl is phenyl.

The reaction may be carried out in a solvent which may include water or an organic solvent such as methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

The reaction mass may be heated to the reflux temperature of the solvent.

According to another aspect of the present invention, there is provided a compound of formula (8)

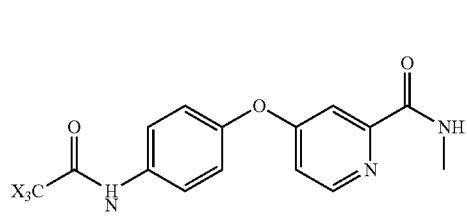

⟨?⟩ indicates text missing or illegible when filed wherein X is halogen. Halogen may be selected from chlorine, bromine or iodine, preferably chlorine.

According to another aspect of the present invention, there is provided a process for preparing a compound of formula (8) comprising reacting 4-(4-aminophenoxy)-N-methylpicolinamide or a salt thereof with a trihaloalkyl halide, a trihaloanhydride, or a trihalo ester

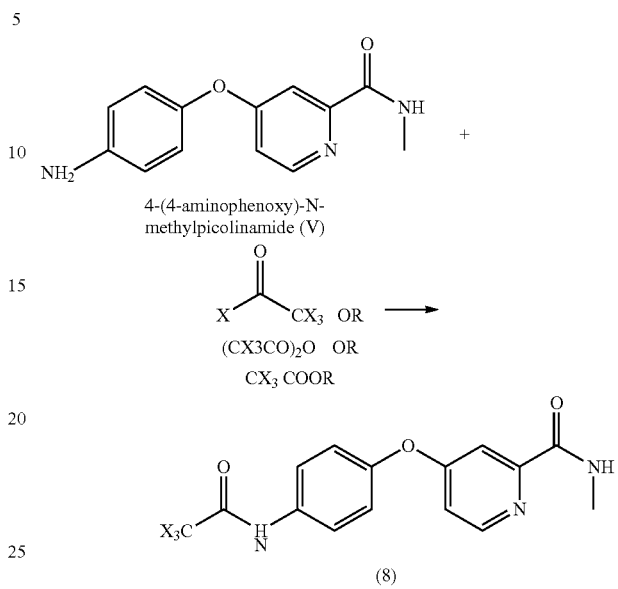

wherein X is halogen, to obtain the compound of formula (8). In an embodiment, the compound (8) is used in the process described above for preparing sorafenib or a salt thereof.

X in trihaloalkyl halide or anhydride or ester is halogen such as chlorine, bromine, iodine, preferably chlorine. The trihaloalkyl halide or anhydride or ester may be selected from the group consisting of trichloroacetyl chloride, tribromoacetyl chloride, trichloroacid anhydride, ethyl trichloroacetate, methyl trichloroacetate, phenyl trichloroacetate, ethyl tribromoacetate.

The trihaloalkyl halide or anhydride or ester is typically added slowly to 4-(4-aminophenoxy)-N-methyl picolinamide so as to maintain the desired temperature of the reaction mass during addition of the trihaloalkyl halide or anhydride or ester. The temperature at which reaction is carried out may range from 0 to 150° C. The reaction is optionally carried out in the presence of a base.

According to another aspect of the present invention, there is provided a process for preparing sorafenib or a salt thereof comprising reacting compound (8) with 4-chloro-3-trifluoromethylaniline

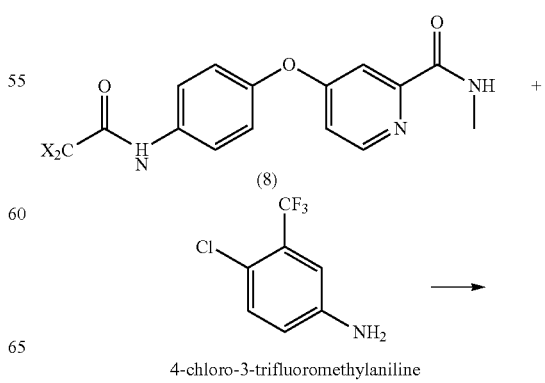

19

-continued

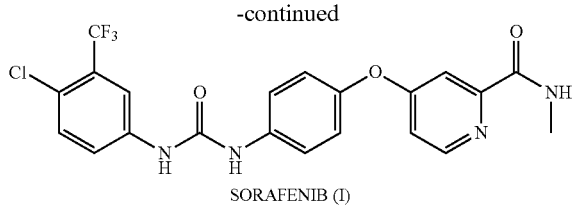

SORAFENIB (I)

wherein X is halogen, in the presence of a base to obtain sorafenib and optionally converting the sorafenib to a salt thereof. In an embodiment, the compound (8) is prepared according to the process described above. X is halogen such as chlorine, bromine, or iodine, preferably chlorine.

The reaction may be carried out in the presence of a solvent which may include organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine, and 1,8-diazabicyclo [5.4.0]undec-7-ene.

In an embodiment, the reaction is carried out at a temperature ranging from 100 to 150° C.

According to another aspect of the present invention, there is provided a process for preparing sorafenib or a salt thereof comprising condensing 4-(4-aminophenoxy)-N-methylpicolinamide or a salt thereof with carbamate derivative (2) (which is the same as carbamate derivative (2) described above)

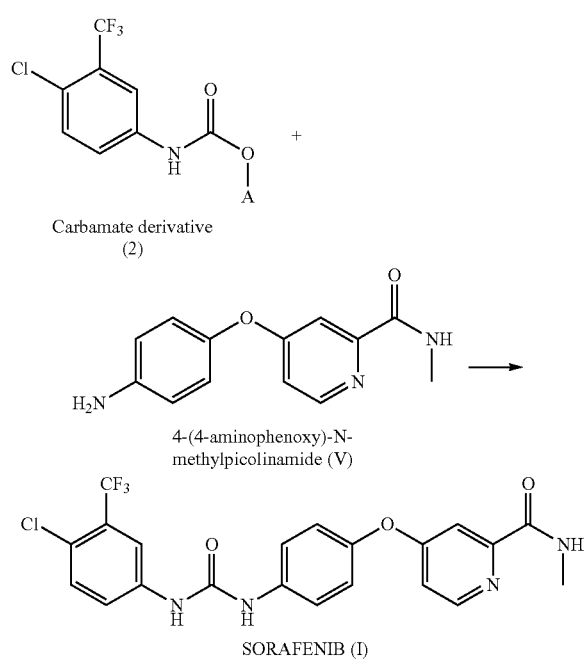

20 wherein A is alkyl or aryl, to obtain sorafenib and optionally converting the sorafenib to a salt thereof. In an embodiment, alkyl is $C_{1-3}$ alkyl, suitably methyl, ethyl, iso-propyl or n-propyl. In another embodiment, aryl is phenyl.

The reaction mass may be stirred at a temperature ranging from 30 to 50° C. to obtain the final product.

The reaction may be carried out in the presence of a solvent which may include organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

In an embodiment, the carbamate derivative (2) is prepared according to the process described above.

According to another aspect of the present invention, there is provided a process for preparing sorafenib or a salt thereof comprising condensing 4-(4-aminophenoxy)-N-methylpicolinamide or a salt thereof with an anilide derivative of formula (3) (which is the same as anilide derivative (3) described above)

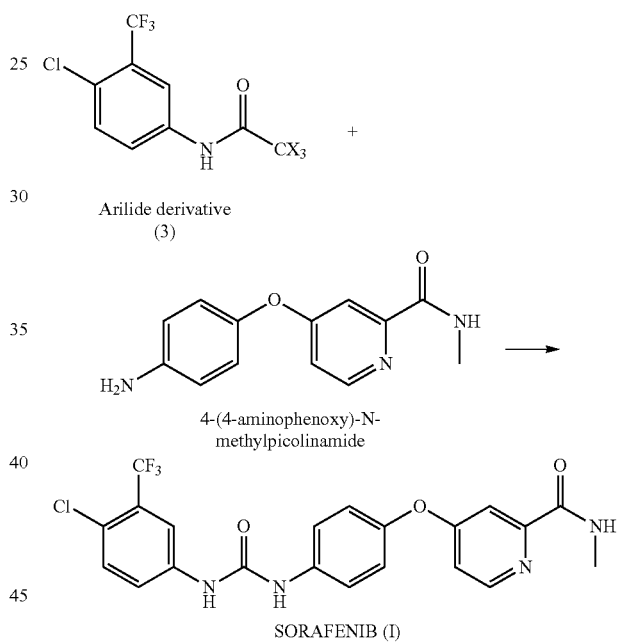

wherein X is halogen, in the presence of a base to obtain sorafenib and optionally converting the sorafenib to a salt thereof. X is halogen such as chlorine, bromine or iodine, preferably chlorine.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine, and 1,8-diazabicyclo [5.4.0]undec-7-ene.

The reaction may be carried out in the presence of a solvent, which may include organic solvent such as water, as methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

The reaction may be carried out at a temperature ranging from 100 to 150° C.

In an embodiment, the anilide derivative (3) is prepared according to the process described above.

According to another aspect of the present invention, there is provided a process for preparing sorafenib or a salt thereof comprising condensing 4-(4-aminophenoxy)-N-methylpicolinamide or a salt thereof with urea derivative (4) (which is the same as the urea derivative (4) described above)

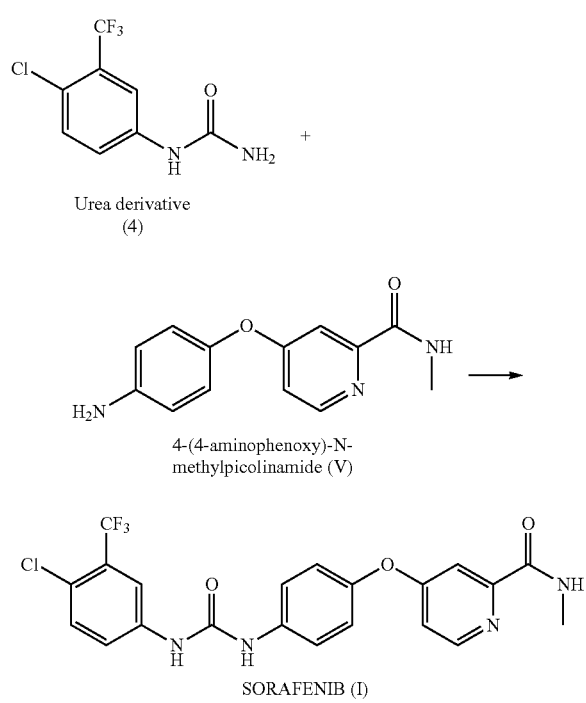

Urea derivative
(4)

4-(4-aminophenoxy)-N-methylpicolinamide (V)

SORAFENIB (I)

in the presence of a base to obtain sorafenib, and optionally converting the sorafenib to a salt thereof.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine, and 1,8-diazabicyclo[5.4.0]undec-7-ene.

The reaction may be carried out in the presence of a solvent, which may include an organic solvent such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

The reaction may be carried out at a temperature ranging from 100 to 150° C.

In an embodiment, the urea derivative (4) is prepared according to the process described above.

According to another aspect of the present invention, there is provided a compound of formula (9)

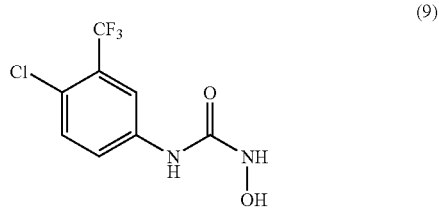 [SMILES: O=C(NO)Nc1ccc(Cl)c(C(F)(F)F)c1]

According to another aspect of the present invention, there is provided a process for preparing hydroxy urea derivative (9) (i.e., the compound (A) in which R' is —C(O)—NHOH) comprising reacting carbamate derivative (2) with a hydroxylamine in a protic solvent.

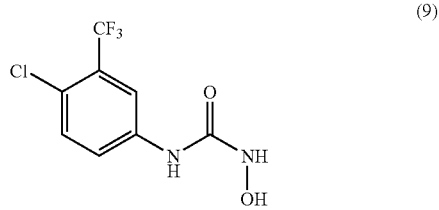 [SMILES: O=C(NO)Nc1ccc(Cl)c(C(F)(F)F)c1]

The hydroxylamine is suitably used as its salt, for example, its hydrochloride salt. Carbamate derivative (2) and the hydroxylamine salt may be mixed and then heated to the reflux temperature of the solvent.

The protic solvent may be selected from acids such as, but not limited to, acetic acid, oxalic acid, benzoic acid, citric acid, succinic acid, benzene sulphonic acid, tartaric acid, methane sulphonic acid, or an inorganic acid. The inorganic acid may be selected from acids such as but not limited to hydrochloric acid, hydrobromic acid, sulphuric acid, nitric acid, or phosphoric acid.

According to another aspect of the present invention, there is provided a process for preparing sorafenib or a salt thereof comprising condensing 4-(4-aminophenoxy)-N-methylpicolinamide or a salt thereof with hydroxylurea derivative (9) (i.e., the compound (A) in which R' is —C(O)—NHOH)

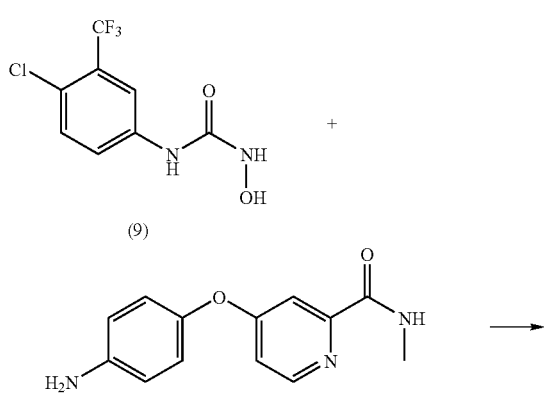

4-(4-aminophenoxy)-N-methylpicolinamide

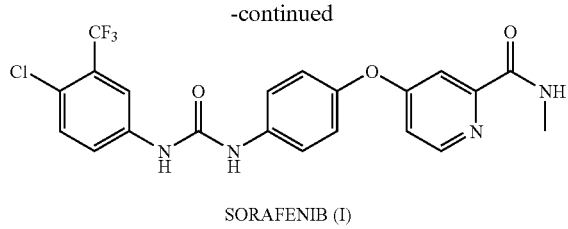

SORAFENIB (I)

to obtain sorafenib, and optionally converting the sorafenib to a salt thereof.

The reaction is typically carried out in the presence of a base. The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine, and 1,8-diazabicyclo [5.4.0]undec-7-ene.

The reaction may be carried out at a temperature ranging from 100 to 150° C.

Sorafenib prepared according to any one of the processes described above forms another aspect of the present invention.

The salt of sorafenib prepared according to any one of the processes described above forms another aspect of the present invention.

According to another aspect of the present invention, there is provided a pharmaceutical composition comprising sorafenib or a salt thereof as prepared according to any one of the processes described above, together with at least one pharmaceutically acceptable excipient. Such pharmaceutical compositions and excipient(s) are well known to those skilled in the art.

According to another aspect of the present invention, there is provided the use of sorafenib or a salt thereof as prepared according to any one of the processes described above in medicine.

According to another aspect of the present invention, there is provided the use of sorafenib or a salt thereof as prepared according to any one of the processes described above in treating renal cell carcinoma or advanced hepatocellular carcinoma.

According to another aspect of the present invention, there is provided the use of sorafenib or a salt thereof as prepared according to any one of the processes described above in the manufacture of a medicament for treating renal cell carcinoma or advanced hepatocellular carcinoma.

According to another aspect of the present invention, there is provided a method for the treatment of renal cell carcinoma or advanced hepatocellular carcinoma comprising administering to a patient in need thereof a therapeutically effective amount of sorafenib or a salt thereof as prepared according to any one of the processes described above.

DETAILED DESCRIPTION OF THE INVENTION

The present invention relates to novel key intermediates useful in the synthesis of sorafenib or its pharmaceutically acceptable salts.

In an embodiment, intermediate (1) of the present invention is obtained by a process comprising the steps of:

a) reacting 3-trifluoromethyl-4-chloroaniline with a haloformate, such as chloroformate, or a carbonate derivative in the presence of a base and a suitable solvent and at a suitable temperature to obtain carbamate derivative (2).

b) reacting carbamate derivative (2) with 4-aminophenol in the presence of a suitable organic solvent to obtain intermediate (1). The reaction is represented by Scheme III.

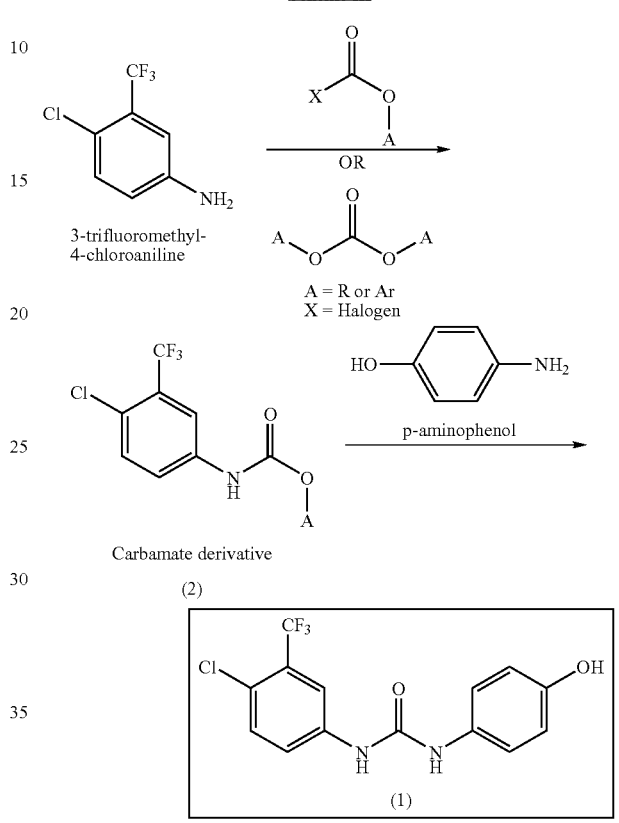

A in the haloformate or carbonate derivative may be alkyl (R) or aryl (Ar) wherein alkyl is $C_{1-3}$ alkyl, suitably methyl, ethyl, iso-propyl or n-propyl, and aryl is preferably phenyl. The carbonate derivative may be an aliphatic or cyclic compound (i.e., the two A groups taken together form a ring). Examples of haloformate or carbonate derivatives which can be used are selected from, but not limited to, phenyl chloroformate, methyl chloroformate, ethyl chloroformate, diethyl carbonate, [1,3]dioxolan-2-one and the like.

The base used may be an organic or inorganic base. The inorganic base may be selected from potassium tertbutoxide, potassium hydroxide, sodium hydroxide, ammonium hydroxide, sodium methoxide, potassium methoxide, potassium carbonate, sodium carbonate, and the like. The organic base may be selected from pyridine, dimethyl amine, triethyl amine, N,N-diisopropylethyl amine, and 1,8-diazabicyclo [5.4.0]undec-7-ene.

The reaction of 3-trifluoromethyl-4-chloroaniline with the haloformate or carbonate derivative may be carried out at a temperature ranging from −10 to 25° C., preferably from −5 to 5° C. Typically, the haloformate or carbonate derivative is added slowly so as to maintain the temperature of the reaction mass.

The reaction of carbamate derivative (2) with 4-aminophenol is carried out at a higher temperature ranging from 0 to 60° C., preferably from 40 to 60° C. wherein the mixture of carbamate derivative and 4-aminophenol is heated to the temperature ranging from 40 to 60° C.

Suitable solvent may include organic solvents such as water, methylene dichloride (MDC), ethylene dichloride, tetrahydrofuran (THF), 1,4-dioxane, methyl isobutyl ketone, ethyl methyl ketone, toluene, N,N-dimethyl formamide (DMF), dimethylsulfoxide (DMSO), ethyl acetate, acetone, acetonitrile, or mixtures thereof.

In another embodiment of the present invention, intermediate (1) may be obtained by the process comprising steps of:

a) reacting 3-trifluoromethyl-4-chloroaniline with a trihaloalkyl halide such as a trihaloalkyl chloride, or a trihaloalkyl anhydride or a trihaloalkyl ester to obtain anilide derivative (3).

b) reacting anilide derivative (3) with 4-aminophenol in a suitable organic solvent at a suitable temperature to obtain intermediate (1). The reaction is represented by Scheme IV.

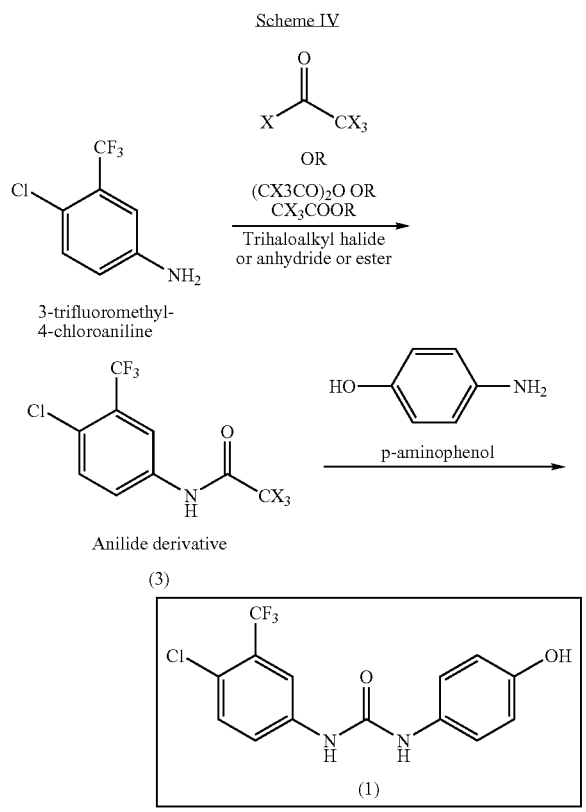

X in trihaloalkyl halide or anhydride or ester is halogen such as chlorine, bromine or iodine, preferably chlorine. R has the same meaning as defined for Scheme III above. The trihaloalkyl halide or anhydride or ester used is selected from, but not limited to, trichloroacetyl chloride, tribromoacetyl chloride, trichloro acid anhydride, ethyl trichloroacetate, methyl trichloroacetate, phenyl trichloroacetate, ethyl tribromoacetate, and the like. The reaction of the trihaloalkyl halide or anhydride or ester is carried out at a temperature ranging from −5 to 25° C. Typically, the trihaloalkyl halide or anhydride or ester is added slowly so as to maintain the desired temperature of the reaction mass during addition of the trihalo compound.

The reaction of anilide derivative (3) with 4-aminophenol is carried out at a higher temperature ranging from 100 to 140° C., preferably from 110 to 120° C. wherein the mixture of anilide derivative and 4-aminophenol is heated to the temperature ranging from 110 to 120° C.

Optionally, the reaction steps are carried out in the presence of a base. The base may be an organic or inorganic base as described for Scheme III above.

The suitable solvent may be an organic solvent as described for Scheme III above.

In an alternative embodiment, intermediate (1) may be made via another process which comprises the steps:

a) reacting 3-trifluoromethyl-4-chloroaniline with an alkali cyanate in acidic conditions at a suitable temperature to obtain urea derivative (4); and b) reacting urea derivative (4) with 4-aminophenol in a suitable organic solvent at a suitable temperature to obtain intermediate (1). The reaction is represented by Scheme V.

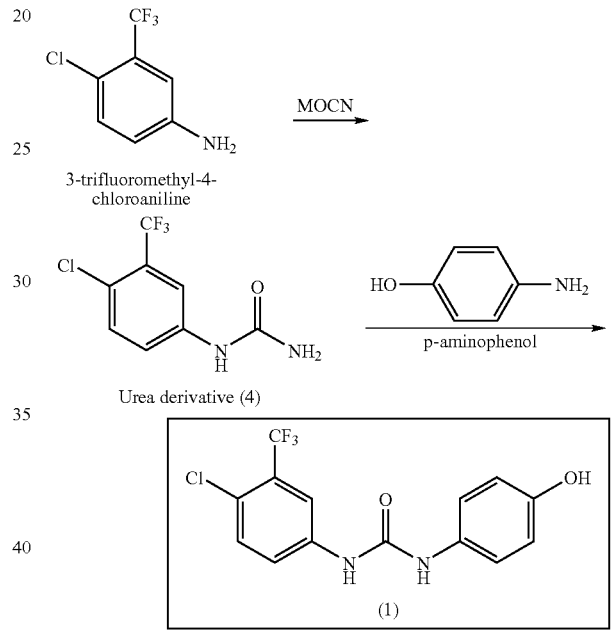

M in the alkali cyanate is an alkali metal such as sodium, potassium, calcium or lithium, preferably sodium. The alkali cyanate is typically added slowly to 3-trifluoromethyl-4-chloroaniline suitably at a temperature ranging from 40 to 50° C. The acid may be an organic or inorganic acid. The organic acid may be selected from acids such as, but not limited to, acetic acid, oxalic acid, benzoic acid, citric acid, succinic acid, benzene sulphonic acid, tartaric acid, or methane sulphonic acid. The inorganic acid may be selected from acids such as, but not limited to, hydrochloric acid, hydrobromic acid, sulphuric acid, nitric acid, or phosphoric acid.

The urea derivative obtained in step a) is mixed with 4-aminophenol and the reaction mass is typically heated to a temperature ranging from 70 to 100° C., preferably from 80 to 90° C.

Suitable solvents used for both the steps are organic solvents as described for Scheme III above.

In yet another embodiment, intermediate (1) may be made via another process which comprises the steps:

a) reacting 4-aminophenol with an alkali cyanate in acidic conditions at a suitable temperature to obtain phenoxy urea (5); and b) reacting phenoxy urea (5) with 3-trifluoromethyl-4-chloroaniline in a suitable organic solvent at a suitable temperature in the presence of a base to obtain intermediate (1). The reaction is represented by Scheme VI.

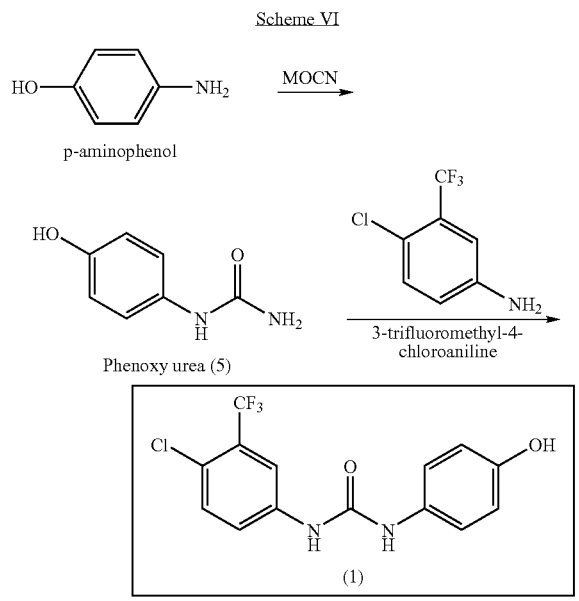

The alkali cyanate and acid used in step a) are the same as described in step a) of Scheme V above. The alkali cyanate is typically added slowly to the 4-aminophenol. The reaction may be carried out at a temperature ranging from 20 to 25° C.

The reaction of the phenoxy urea (5) and 3-trifluoromethyl-4-chloroaniline is suitably carried out at a temperature ranging from 100 to 150° C. The base and the solvents used are the same as described for Scheme III above.

In another embodiment, there is provided an intermediate of formula (1).

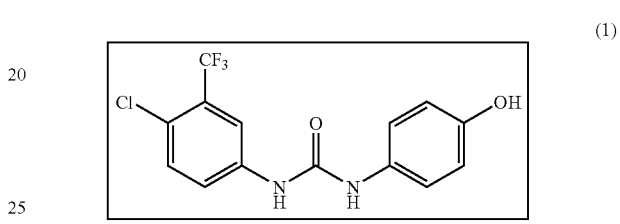

A schematic representation of various processes for the preparation of novel intermediate (1) is as follows:

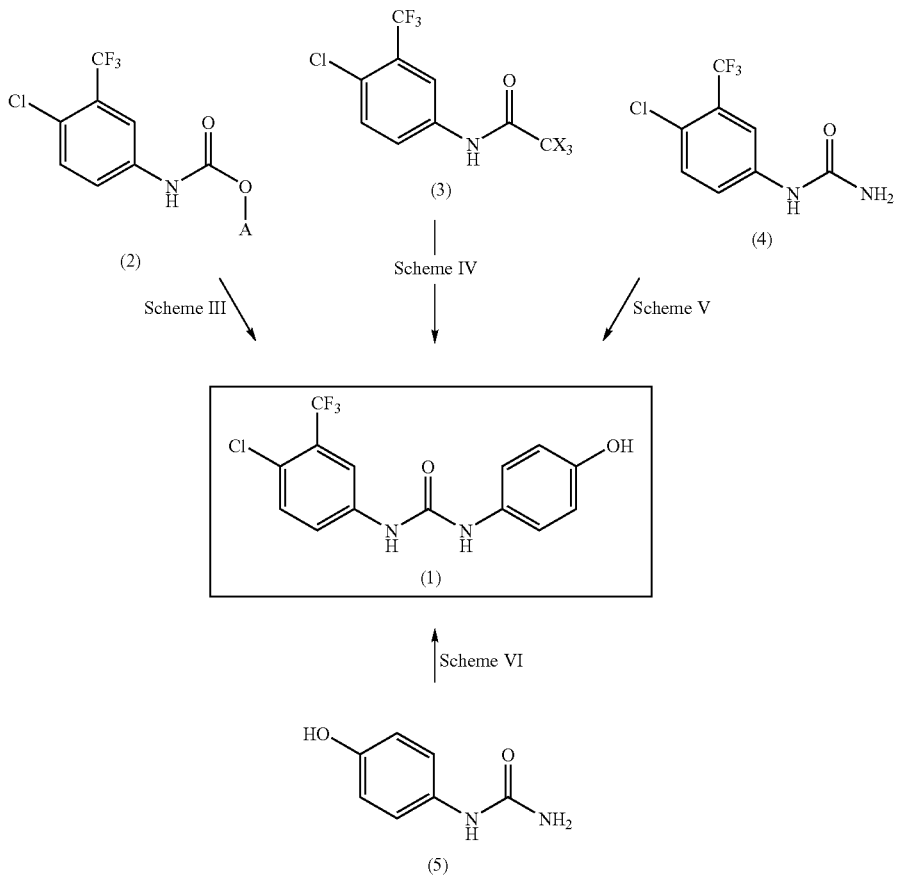

In another aspect of the present invention, intermediate (1) is used in the synthesis of sorafenib. In an embodiment, intermediate (1) is reacted with 4-chloro-N-methyl-2-pyridine carboxamide in the presence of a base at a suitable temperature. The reaction is represented by Scheme VII.

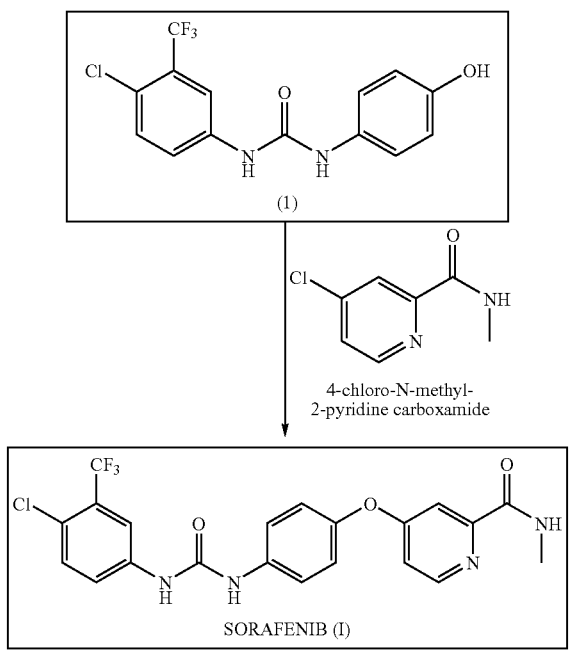

The base may be the same as that described for Scheme III above. The reaction may be carried out at a temperature ranging from 20 to 80° C.

The advantage of this process is that it gives a good yield and purity of sorafenib.

According to another aspect of the present invention, there is provided novel intermediate (6).

According to another aspect of the present invention, intermediate (6) is used in the preparation of sorafenib. In an embodiment, the process comprises the steps of:

a) reacting 4-(4-aminophenoxy)-N-methylpicolinamide or a salt thereof with an alkali cyanate in the presence of a protic solvent at a suitable temperature to obtain intermediate (6); and b) reacting intermediate (6) with 3-trifluoromethyl-4-chloroaniline in the presence of a base and an organic solvent at a suitable temperature to obtain sorafenib. The reaction is represented by Scheme IIIa below.

M in the alkali cyanate in Scheme Ma is an alkali metal such as sodium, potassium, calcium or lithium, preferably sodium. The protic solvent may be selected from acids such as but not limited to acetic acid, oxalic acid, benzoic acid, citric acid, succinic acid, benzene sulphonic acid, tartaric acid, methane sulphonic acid, or an inorganic acid. The inorganic acid may be selected from acids such as, but not limited to, hydrochloric acid, hydrobromic acid, sulphuric acid, nitric acid, or phosphoric acid.

The alkali cyanate may be added to 4-(4-aminophenoxy)-N-methylpicolinamide or its salt at 20-25° C. The addition of alkali cyanate to 4-(4-aminophenoxy)-N-methylpicolinamide is typically carried out slowly so as to maintain the desired temperature of the reaction mass during addition of the alkali cyanate. After addition, the reaction mass may be stirred to obtain intermediate (6).

Intermediate (6) is then reacted with 3-trifluoromethyl-4-chloroaniline in the presence of a base such as but not limited to potassium tert.butoxide, potassium hydroxide, sodium hydroxide, ammonium hydroxide, sodium methoxide, potassium methoxide, potassium carbonate, sodium carbonate, pyridine, dimethyl amine, triethylamine, N,N-diisopropylethyl amine or 1,8-diazabicyclo[5.4.0]undec-7-ene. The suitable solvent may be an organic solvent such as water, methylene dichloride (MDC), ethylene dichloride, tetrahydrofuan (THF), 1,4-dioxane, methylisobutyl ketone, ethylmethyl ketone, toluene, N,N-dimethylformamide (DMF), dimethylsulfoxide (DMSO), ethyl acetate, acetone, acetonitrile, or mixtures thereof.

The reaction mass may be heated to the reflux temperature of the solvent.

In another embodiment of the present invention, sorafenib is prepared by a process comprising the steps:

a) reacting 4-(4-aminophenoxy)-N-methylpicolinamide or a salt thereof with a haloformate such as chloroformate or a carbonate derivative in the presence of a base at a suitable temperature to obtain intermediate (7); and b) reacting intermediate (7) with 3-trifluoromethyl-4-chloroaniline to obtain sorafenib.

The reaction is represented by Scheme IVa below.

4-(4-aminophenoxy)-N-methylpicolinamide is reacted with a haloformate or a carbonate derivative in the presence of the base typically at a temperature ranging from −5 to 25° C. preferably from 0 to 5° C.

A in the haloformate or carbonate derivative may be alkyl (R) or aryl (Ar) wherein alkyl is $C_{1-3}$ alkyl, suitably methyl, ethyl, iso-propyl or n-propyl, and aryl is preferably phenyl. The carbonate derivative may be an aliphatic or cyclic compound (i.e., the two A groups taken together form a ring). Examples of haloformate or carbonate derivatives which can be used are selected from but not limited to phenyl chloroformate, methyl chloroformate, ethyl chloroformate, diethyl carbonate, [1,3]dioxolan-2-one, and the like.

The base used is the same as the base described for Scheme IIIa above.

Intermediate (7) is then mixed with 3-trifluoromethyl-4-chloroaniline in an organic solvent in the same way as described above in relation to Scheme IIIa. The reaction mass may be heated to the reflux temperature of the solvent.

In yet another embodiment of the present invention, sorafenib may also be prepared by a process comprising the steps:

a) reacting 4-(4-aminophenoxy)-N-methylpicolinamide or a salt thereof with a trihaloalkyl halide for example a trihaloalkyl chloride, or a trihaloanhydride or a trihalo ester at a suitable temperature to obtain intermediate (8); and b) reacting intermediate (8) with 3-trifluoromethyl-4-chloroaniline to obtain sorafenib. The reaction is represented by Scheme Va.

X in trihaloalkyl halide or anhydride or ester is halogen such as chlorine, bromine, iodine, preferably chlorine. The trihaloalkyl halide or anhydride or ester may be selected from the group consisting of trichloroacetyl chloride, tribromoacetyl chloride, trichloroacid anhydride, ethyl trichloroacetate, methyl trichloroacetate, phenyl trichloroacetate, ethyl tribromoacetate.

The trihaloalkyl halide or anhydride or ester is typically added slowly to 4-(4-aminophenoxy)-N-methyl picolinamide so as to maintain the desired temperature of the reaction mass during addition of the trihalo compound. The temperature at which reaction is carried out may range from 0 to 150° C. The reaction is optionally carried out in the presence of a base.

Intermediate (8) is then mixed with 3-trifluoromethyl-4-chloroaniline in an organic solvent in the same way as described above in relation to Scheme IIIa typically at an elevated temperature ranging from 100 to 150° C. The reaction is carried out in presence of a base. The base used is the same as described in relation to Scheme IIIa above.

ate derivative (2). The solvent used in the reaction is the same as described above in relation to Scheme IIIa above. The reaction mass may be stirred at a temperature ranging from 30 to 50° C. to obtain the final product. The reaction is represented by Scheme VIa. The carbamate derivative (2) is the same as the carbamate derivative used in Scheme III above.

The carbamate derivative (2) may be prepared by reacting 3-trifluoromethyl-4-chloroaniline with a haloformate such as a chloroformate or carbonate derivative in the presence of a

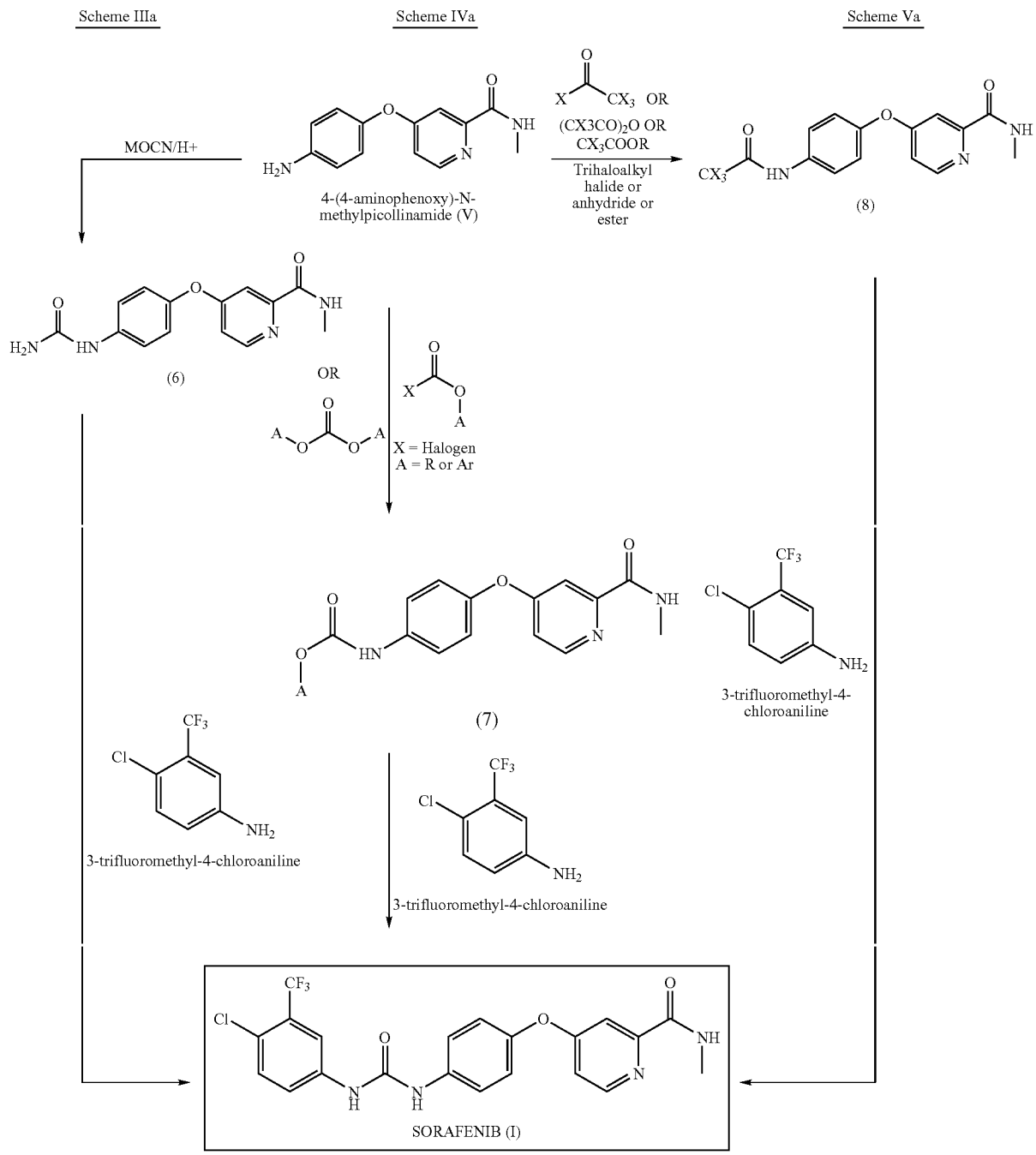

In another embodiment of the present invention, sorafenib is alternatively prepared by condensing 4-(4-aminophenoxy)-N-methylpicolinamide or a salt thereof with a carbamate base as described in relation to Scheme IIIa above. Addition of the haloformate or carbonate derivative to 3-trifluoromethyl-4-chloroaniline is typically carried out slowly so as to maintain the desired temperature of the reaction mass during addition of the alkali cyanate. The temperature at which reaction is carried out may be in the range from −10 to 25° C.

In yet another embodiment of the present invention sorafenib is alternatively prepared by condensing 4-(4-aminophenoxy)-N-methylpicolinamide with a urea derivative (4) in the presence of a base. The reaction may involve mixing 4-(4-aminophenoxy)-N-methylpicolinamide or a salt thereof with urea derivative (4) in a suitable solvent at a temperature ranging from 100 to 150° C. Further, the reaction is carried out in presence of a base. The base and the solvent used are the same as described in relation to Scheme IIIa above. The reaction is represented by Scheme VIIa. The urea derivative (4) is the same as the urea derivative used in Scheme V above.

Urea derivative (4) may be prepared by reacting 3-trifluoromethyl-4-chloroaniline or an acid addition salt thereof with an alkali cyanate in the presence of a protic solvent. The alkali cyanate and protic solvent are the same as described above in relation to Scheme IIIa. The alkali cyanate is typically added slowly to 3-trifluoromethyl-4-chloroaniline at a temperature ranging from 40 to 50° C.

In yet another alternative embodiment of the present invention sorafenib is alternatively prepared by condensing 4-(4-aminophenoxy)-N-methylpicolinamide or a salt thereof with anilide derivative (3). Typically, the reaction is carried out in a suitable solvent and in the presence of a base optionally at a temperature ranging from 100 to 150° C. The solvent and the base used is the same as described above in relation to Scheme IIIa. The reaction is represented by Scheme VIIIa. The anilide derivative (3) is the same as the anilide derivative used in Scheme IV above.

Anilide derivative (3) may be obtained by reacting 3-trifluoromethyl-4-chloroaniline with a trihaloalkyl halide such as a trihaloalkyl chloride or a trihaloanhydride or a trihalo ester. The reaction of the trihaloalkyl halide or anhydride or ester is typically carried out at a temperature ranging from −5 to 25° C. Suitably, the trihaloalkyl halide or anhydride or ester is added slowly so as to maintain a constant temperature of the reaction mass during addition of the trihaloalkyl halide or anhydride or ester. Optionally the reaction is carried out in presence of a base. The base and the solvent used are the same as described above in relation to Scheme IIIa.

In yet another embodiment of the present invention, sorafenib is prepared by condensing 4-(4-aminophenoxy)-N-methylpicolinamide or a salt thereof with hydroxy urea derivative (9). The reaction is typically carried out in the presence of a base as described above in relation to Scheme IIIa and optionally at a temperature ranging from 100 to 150° C. The reaction is represented by Scheme IX.

Hydroxy urea derivative (9) may be obtained by reacting carbamate derivative (2) with a hydroxylamine in a protic solvent. The hydroxylamine is suitably used as its salt, for example, its hydrochloride salt. Carbamate derivative (2) and the hydroxylamine salt may be mixed and then heated to the reflux temperature of the solvent. The protic solvent is the same as described above in relation to Scheme IIIa.

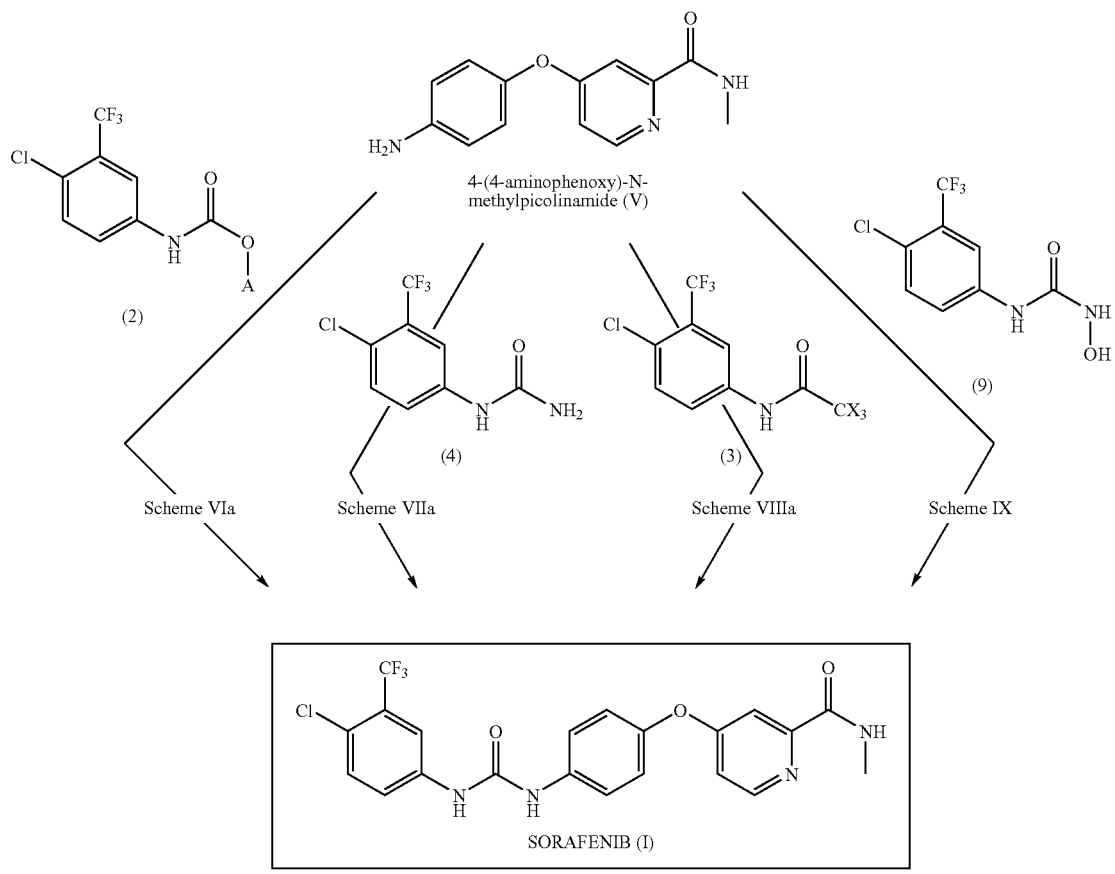

The synthesis of intermediates (2), (3) and (4) is shown below in Scheme X.

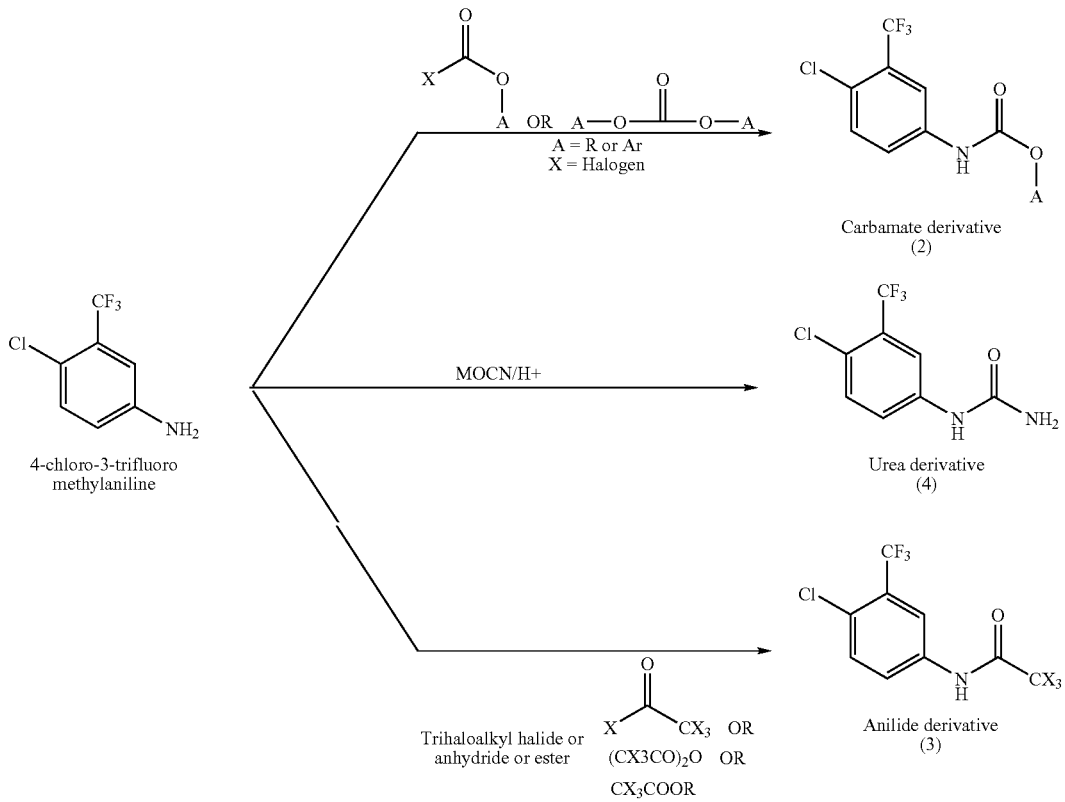

The synthesis of intermediate (9) is shown below in Scheme XI.

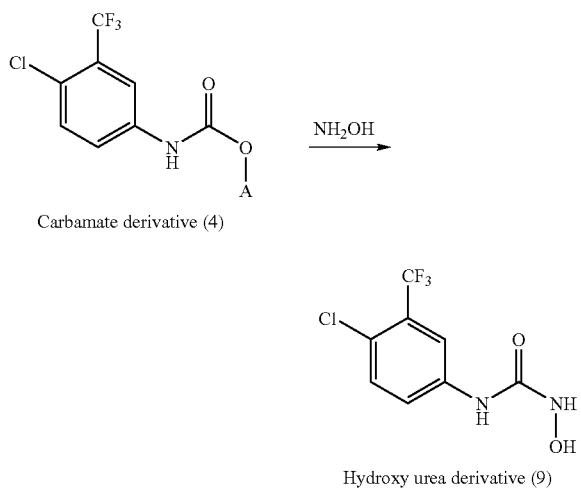

Optionally, the sorafenib may be converted into a pharmaceutically acceptable salt thereof, more specifically into its tosylate salt. The tosylate salt of sorafenib may be prepared by reaction with p-toluene sulfonic acid.

EXAMPLES

The present invention is now further illustrated by the following examples, which do not, in any way, limit the scope of the invention.

Example 1

Synthesis of phenyl 4-chloro-3-(trifluoromethyl)phenylcarbamate (Compound 2)

3-trifluoromethyl-4-chloroaniline (25 g, 0.1278 mol) and pyridine (26 ml, 0.3195 mol) were dissolved in dichloromethane (250 ml). The reaction mass was cooled to 0° C. to −5° C. and a solution of phenyl chloroformate (22 ml, 0.1661 mol) in dichloromethane (100 ml) was added drop wise maintaining the temperature of the reaction mass below 0° C. The reaction mass was stirred at 0° C. to 5° C. for 1-2 hours and quenched with water (200 ml) below 10° C. The organic phase was separated and washed with water followed by 1N HCl. It was then dried over sodium sulfate and concentrated to obtain solid. This solid was agitated with hexane (350 ml) at ambient temperature for 2-3 hours and filtered. The obtained product was vacuum dried at 50° C. to give phenyl 4-chloro-3-(trifluoromethyl)phenylcarbamate (36 g) as white solid.

Example 2

Synthesis of 1-(4-chloro-3-(trifluoromethyl)phenyl)-3-(4-hydroxyphenyl)urea (Compound 1)

To the dry N,N-dimethyl formamide (150 ml) phenyl 4-chloro-3-(trifluoromethyl)phenylcarbamate (50 g, 0.15873 mol) and p-amino phenol (20.78 g, 0.1904 mol) were added at room temperature. The reaction mass was then heated to 50° C. for 4-6 hours and cooled to room temperature. Water (500 ml) was added and the obtained mass was extracted with ethyl acetate and the combined extracts were washed with water. It was dried over sodium sulfate and concentrated to obtain semi solid. The residue was then charged with acetonitrile (700 ml) and the obtained precipitate was stirred at ambient temperature for 2-3 hours. The solid was filtered and washed thoroughly with acetonitrile till clear filtrate was obtained. The solid thus obtained was dried in vacuum oven at 50° C. to afford the desired 1-(4-chloro-3-(trifluoromethyl)phenyl)-3-(4-hydroxyphenyl)urea (40 g).

Example 3

Synthesis of 2,2,2-trichloro-N-(4-chloro-3-(trifluoromethyl)phenyl)acetamide (Compound 3)

The clear solution of 3-trifluoromethyl-4-chloroaniline (35 g, 0.1789 mol) and pyridine (36 ml, 0.447 mol) in dichloromethane (350 ml) was cooled at 0° C. to −5° C. and a solution of trichloro acetyl chloride (26 ml, 0.2326 mol) in dichloromethane (75 ml) was added drop wise maintaining temperature of the reaction mass below 0° C. The reaction mass was stirred for 1 hour below 0° C. and quenched with water (150 ml) below 5° C. The organic phase was separated and aqueous layer was reextracted with dichloromethane. The combined dichloromethane layer was then washed with water, dried over sodium sulfate and evaporated under vacuum to obtain (55 g) the desired product, i.e., 2,2,2-trichloro-N-(4-chloro-3-(trifluoromethyl)phenyl)acetamide.

Example 4

Synthesis of 2,2,2-trichloro-N-(4-chloro-3-(trifluoromethyl)phenyl)acetamide (Compound 3)

The clear solution of 3-trifluoromethyl-4-chloroaniline (35 g, 0.1789 mol) and pyridine (36 ml, 0.447 mol) in dichloromethane (350 ml) was cooled at 0° C. to −5° C. and a solution of trichloro acid anhydride (42.8 ml, 0.2345 mol) in dichloromethane (75 ml) was added drop wise maintaining temperature of the reaction mass below 0° C. The reaction mass was stirred for 1 hour below 0° C. and quenched with water (150 ml) below 5° C. The organic phase was separated and aqueous layer was reextracted with dichloromethane. The combined dichloromethane layer was then washed with water, dried over sodium sulfate and evaporated under vacuum to obtain (52 g) the desired product, i.e., 2,2,2-trichloro-N-(4-chloro-3-(trifluoromethyl)phenyl)acetamide.

Example 5

Synthesis of 2,2,2-trichloro-N-(4-chloro-3-(trifluoromethyl)phenyl)acetamide (Compound 3)

3-trifluoromethyl-4-chloroaniline (50 g, 0.255 mol) was mixed with ethyl-2,2,2-trichloro acetate (150 ml) in toluene (500 ml) at room temperature. The mixture was refluxed for 2-3 hours. The organic solvent was degassed under reduced pressure to obtain oil. This oil was stirred with hexane to obtain the desired product (79 g), i.e., 2,2,2-trichloro-N-(4-chloro-3-(trifluoromethyl)phenyl)acetamide.

Example 6

Synthesis of 1-(4-chloro-3-(trifluoromethyl)phenyl)-3-(4-hydroxyphenyl)urea (Compound 1)

2,2,2-trichloro-N-(4-chloro-3-(trifluoromethyl)phenyl)acetamide (25 g, 0.07338 mol) was dissolved in dimethyl formamide (75 ml). 1,8-diazabicyclo[5.4.0]undec-7-ene (17.5 ml, 0.11731 mol) and 4-amino phenol (9.6 g, 0.0879 mol) were added in one lot. The reaction mass was heated to 110-120° C. for 18-20 hours, cooled to room temperature and quenched in water (750 ml). The quenched mass was extracted repeatedly with ethyl acetate and the combined ethyl acetate layer was then back washed with water. It was then dried over sodium sulfate and evaporated under vacuum to obtain solid. The obtained solid was slurried in acetonitrile (300 ml) at ambient temperature and filtered to give 1-(4-chloro-3-(trifluoromethyl)phenyl)-3-(4-hydroxyphenyl)urea (18 g).

Example 7

Synthesis of 1-(4-chloro-3-(trifluoromethyl)phenyl)urea (Compound 4)

Sodium cyanate (1.7 g, 0.02 mol) was dissolved in water (17 ml) at room temperature to obtain a clear solution. This solution was then charged drop wise to the clear solution of 3-trifluoromethyl-4-chloro aniline (5 g, 0.025 mol) in acetic acid (25 ml) at 40° C.-45° C. within 1-2 hours. The reaction mass was then agitated for whole day cooling gradually to room temperature. The obtained solid was then filtered, washed with water and vacuum dried at 50° C. to afford (4.5 g) the desired product, i.e., 1-(4-chloro-3-(trifluoromethyl)phenyl)urea.

Example 8

Synthesis of 1-(4-chloro-3-(trifluoromethyl)phenyl)-3-(4-hydroxyphenyl)urea (Compound 1)

1-(4-chloro-3-(trifluoromethyl)phenyl)urea (100 g, 0.04191 mol), 1,8-diazabicyclo[5.4.0]undec-7-ene (9.4 ml, 0.0628 mol) and 4-amino phenol (5.48 g, 0.050 mol) were mixed with dimethyl sulfoxide (25 ml) and the reaction mass was heated to 80°-90° C. for 8-9 hours. It was then cooled to room temperature and quenched in water (150 ml). The quenched mass was extracted repeatedly with ethyl acetate and the combined ethyl acetate layer was then back washed with water. The residue was then dried over sodium sulfate and evaporated under vacuum to obtain solid. The solid thus obtained was then slurried in acetonitrile (100 ml) at ambient temperature and filtered. It was washed repeatedly with acetonitrile till clear filtrate was obtained. The obtained cake was suck dried for 10 minutes and vacuum dried at 50° C. to give 1-(4-chloro-3-(trifluoromethyl)phenyl)-3-(4-hydroxyphenyl)urea (9.8 g).

Example 9

Synthesis of 1-(4-hydroxyphenyl)urea (Compound 5)

4-aminophenol (45 g, 0.4123 mol) was charged in water and acetic acid mixture (9:1) (450 vol) to obtain a clear solution. To this clear solution was added drop wise previously prepared solution of sodium cyanate (29.48 g, 0.45358 mol) in water over a period of 1 hour. The reaction mass obtained was stirred for 6 hours at ambient temperature and filtered to obtain solid. The solid was washed with water and vacuum dried to obtain the desired product, i.e., 1-(4-hydroxyphenyl)urea (48 g).

Example 10

Synthesis of 1-(4-chloro-3-(trifluoromethyl)phenyl)-3-(4-hydroxyphenyl)urea (Compound 1)

To the dry N,N-dimethylformamide (45 ml) and 1-(4-hydroxyphenyl)urea (15 g, 0.0985 mol) solution were added triethylamine (34 ml, 0.24646 mol) and 3-trifluoromethyl-4-chloroaniline (19.28 g, 0.0985 mol) in one lot. This reaction mass was then agitated at 100° C. for 10-12 hours, quenched in water and the aqueous layer was extracted with ethyl acetate. The ethyl acetate layer was back washed with water and dried over sodium sulfate. It was evaporated under vacuum to obtain solid. The obtained solid was slurried in acetonitrile (100 ml) at ambient temperature, filtered and washed repeatedly with acetonitrile till the clear filtrate was obtained. The obtained cake was then suck dried for 10 minutes and vacuum dried at 50° C. to give 1-(4-chloro-3-(trifluoromethyl)phenyl)-3-(4-hydroxyphenyl)urea (25 g).

Example 11

Synthesis of 4-(4-{3-[4-Chloro-3-(trifluoromethyl)phenyl]ureido}phenoxy)-$N^2$-methylpyridine-2-carboxamide (Compound I—sorafenib)

1-(4-chloro-3-(trifluoromethyl)phenyl)-3-(4-hydroxyphenyl)urea (35 g, 0.1060 mol) was dissolved in dry N,N-dimethyl formamide (100 ml) and potassium tert-butoxide (14.28 g, 0.1272 mol) was added in one lot at room temperature. The reaction mass was stirred at ambient temperature for 2-3 hours and 4-chloro-N-methyl picolinamide (18.09 g, 0.1060 mol) was added in one lot. The reaction mass was maintained at 60-70° C. for 2-3 hours and cooled to room temperature. It was then diluted with ethyl acetate and the organic layer was washed with water followed by 1N HCl and finally with brine. The organic layer was separated, dried over sodium sulfate and degassed to obtain solid. The obtained solid was stripped with ethyl acetate, finally slurried in acetonitrile (350 ml) at room temperature, filtered and vacuum dried to give 4-(4-{3-[4-Chloro-3-(trifluoromethyl)phenyl]ureido}phenoxy)-$N^2$-methylpyridine-2-carboxamide (sorafenib) (32 g).

Example 12

Synthesis of Sorafenib Tosylate (Compound VII)

4-(4-{3-[4-chloro-3-(trifluoromethyl)phenyl]ureido}phenoxy)-$N^2$-methylpyridine-2-carboxamide (sorafenib) (50 g, 0.1075 mol) was suspended in acetone (500 ml) at ambient temperature. p-toluene sulfonic acid (25 g, 0.1398 mol) was dissolved in acetone (250 ml) and this solution was charged to above reaction mass drop wise in 15 minutes and the obtained precipitate was stirred for 1-2 hours at ambient temperature, filtered and washed with acetone (100 ml). It was then vacuum dried for 12 hours at 50° C. to afford 4-4-(4-{3-[4-Chloro-3-(trifluoromethyl)phenyl]ureido}phenoxy)-$N^2$-methylpyridine-2-carboxamide tosylate (sorafenib tosylate) (65 g).

Example 13

Synthesis of N-methyl-4-(4-ureidophenoxy)picolinamide (Compound 6)

A solution of sodium cyanate (5.5 g, 0.0846 mol) in water (55 ml) was prepared. This clear solution was then added to the stirred solution of 4-(4-aminophenoxy)-N-methylpicolinamide hydrochloride (V) (25 g, 0.0894 mol) in water (125 ml) drop wise maintaining ambient temperature of the reaction mass. The reaction mass was then stirred for 24 hours at the same temperature and the obtained solid was then filtered, washed thoroughly with water and vacuum dried at 80° C. to obtain (16 g) of the N-methyl-4-(4-ureidophenoxy)picolinamide.

Example 14

Synthesis of Sorafenib

N-methyl-4-(4-ureidophenoxy)picolinamide (50 g, 0.1746 mol), 1,8-diazabicyclo[5.4.0]undec-7-ene (33.95 ml, 0.2270 mol) and 3-trifluoromethyl-4-chloroaniline (34.2 g, 0.1746 mol) were mixed with N,N-dimethyl formamide (200 ml) (DMF) and the reaction mass was heated to reflux for 24 hours. It was then cooled to room temperature and quenched in water (600 ml). The quenched mass was extracted repeatedly with ethyl acetate and the combined ethyl acetate layer was then back washed with water to remove DMF traces. It was then dried over sodium sulfate and evaporated under vacuum to obtain solid. The solid thus obtained was then slurried in ethyl acetate (400 ml) at ambient temperature and filtered to give 4-(4-(3-(4-chloro-3-(trifluoromethyl)phenyl)ureido)phenoxy)-N-methylpicolinamide (sorafenib base) (64 g).

Example 15

Synthesis of phenyl 4-(2-(methylcarbamoyl)pyridin-4-yloxy)phenylcarbamate (Compound 7)

4-(4-aminophenoxy)-N-methylpicolinamide (35 g, 0.1440 mol) was dissolved in dichloromethane (350 ml) and pyridine (64 ml) was added to the reaction mass at ambient temperature. The reaction mass was then cooled to 0° C. to −5° C. and a solution of phenyl chloroformate (23.5 ml, 0.180 mol) in dichloromethane (125 ml) was added drop wise maintaining the temperature of the reaction mass below 0° C. The reaction was stirred at 0° C. to 5° C. for 1-2 hours and quenched with water (200 ml) below 10° C. The organic phase was separated, washed with water followed by 1N HCl (100 ml) and dried over sodium sulfate and then concentrated to obtain solid. This solid was agitated with hexane (350 ml) at ambient temperature for 2-3 hours and filtered. The obtained product was vacuum dried at 50° C. to give 4-(2-(methylcarbamoyl)pyridin-4-yloxy)phenylcarbamate (48 g) as pale yellow solid.

Example 16

Synthesis of Sorafenib

A mixture of 4-(2-(methylcarbamoyl)pyridin-4-yloxy) phenylcarbamate (25 g, 0.06871 mol) and 3-trifluoromethyl-4-chloroaniline (13.4 g, 0.06871 mol) in acetonitrile (250 ml) was refluxed for 24 hours when product precipitated out of reaction mass. The reaction mass was cooled to room temperature and obtained product was filtered, washed with acetonitrile till a clear filtrate was obtained. It was then vacuum dried to obtain 4-(4-(3-(4-chloro-3-(trifluoromethyl) phenyl)ureido)phenoxy)-N-methylpicolinamide (sorafenib base) (28 g).

Example 17

Synthesis of N-methyl-4-(4-(2,2,2-trichloroacetamido)phenoxy)picolinamide (Compound 8)

The clear solution of 4-(4-aminophenoxy)-N-methylpicolinamide (100 g, 0.411 mol) in dichloromethane (100 ml) was cooled to 0° C. to −5° C. and pyridine (83 ml, 1.02 mol) was added in one lot to the reaction mass. It was then agitated at same temperature for 15 minutes and a solution of trichloroacetyl chloride (60 ml, 0.535 mol) in dichloromethane (500 ml) was added dropwise maintaining temperature of the reaction mass below 0° C. The reaction mass was then stirred for 2-3 hours below 0° C. and quenched with water (500 ml) below 5° C. The organic phase was then separated and aqueous layer was reextracted with dichloromethane. The combined dichloromethane layer was washed with water, dried over sodium sulfate and evaporated under vacuum to obtain (72 g) of the desired product.

Example 18

Synthesis of N-methyl-4-(4-(2,2,2-trichloroacetamido)phenoxy)picolinamide (Compound 8)

The clear solution of 4-(4-aminophenoxy)-N-methylpicolinamide (100 g, 0.411 mol) in dichloromethane (100 ml) was cooled to 0° C. to −5° C. and pyridine (83 ml, 1.02 mol) was added in one lot to the reaction mass. It was then agitated at same temperature for 15 minutes and a solution of trichloroacid anhydride (98 ml, 0.535 mol) in dichloromethane (500 ml) was added dropwise maintaining temperature of the reaction mass below 0° C. The reaction mass was then stirred for 2-3 hours below 0° C. and quenched with water (500 ml) below 5° C. The organic phase was then separated and aqueous layer was re-extracted with dichloromethane. The combined dichloromethane layer was washed with water, dried over sodium sulfate and evaporated under vacuum to obtain (70 g) of the desired product.

Example 19

Synthesis of N-methyl-4-(4-(2,2,2-trichloroacetamido)phenoxy)picolinamide (Compound 8)

4-(4-aminophenoxy)-N-methylpicolinamide (35 g, 0.144 mol) was mixed with ethyl-2,2,2-trichloroacetate (50 ml, 0.27 mol) in toluene (350 ml) at ambient temperature. The mixture was then heated to 100° C. under distillation mode for 2-3 hours. The organic solvent was degassed under reduced pressure to obtain oil. This oil was triturated with hexane (500 ml) to obtain (49 g) of the desired solid.

Example 20

Synthesis of Sorafenib

N-methyl-4-(4-(2,2,2-trichlorochloroacetamido)phenoxy)picolinamide (25 g, 0.0644 mol) was dissolved in N,N-dimethyl formamide (75 ml). 1,8-Diazabicyclo[5.4.0]undec-7-ene (11.35 ml, 0.0805 mol) and 3-trifluoromethyl-4-chloroaniline (12.60 g, 0.0644 mol) were added in one lot. The reaction mass was then heated to 110° C. for 8-9 hours, cooled to room temperature and quenched in water (250 ml). The quenched mass was extracted repeatedly with ethyl acetate and the combined ethyl acetate layer was back washed with water to remove DMF traces. It was dried over sodium sulfate and evaporated under vacuum to obtain solid. The obtained solid was slurried in ethyl acetate (350 ml) at ambient temperature and filtered to give 4-(4-(3-(4-chloro-3-(trifluoromethyl)phenyl)ureido)phenoxy)-N-methylpicolinamide (sorafenib base) (20 g).

Example 21

Synthesis of phenyl 4-chloro-3-(trifluoromethyl)phenylcarbamate (Compound 2)

3-trifluoromethyl-4-chloroaniline (55 g, 0.281 mol) and pyridine (56 ml, 0.7030 mol) were dissolved in dichloromethane (550 ml). The reaction mass was cooled to 0° C. to −5° C. and a solution of phenyl chloroformate (46 ml, 0.3515 mol) in dichloromethane (200 ml) was added drop wise maintaining the temperature of the reaction mass below 0° C. The reaction mass was stirred at 0° C. to 5° C. for 1-2 hours and quenched with water (250 ml) below 10° C. The organic phase was separated and washed with water followed by 1N HCl (100 ml). It was dried over sodium sulfate and concentrated to obtain solid. This solid was agitated with hexane (500 ml) at ambient temperature for 2-3 hours and filtered. The obtained product was then vacuum dried at 50° C. to give phenyl 4-chloro-3-(trifluoromethyl)phenylcarbamate (85 g) as white solid.

Example 22

Synthesis of Sorafenib

Phenyl 4-chloro-3-(trifluoromethyl)phenylcarbamate (100 g, 0.3174 mol) and 4-(4-aminophenoxy)-N-methylpicolinamide (77.14 g, 0.3174 mol) were dissolved in N,N-dimethyl formamide (300 ml) to obtain a clear reaction mass. The reaction mass was agitated at 40-45° C. for 2-3 hours, cooled to room temperature and diluted with ethyl acetate (1000 ml). The organic layer was washed with water (250 ml) followed by 1N HCl (250 ml) and finally with brine (250 ml). The organic layer was separated, dried over sodium sulfate and degassed to obtain solid. This solid was stripped with ethyl acetate and finally slurried in ethyl acetate (1000 ml) at room temperature. It was then filtered and vacuum dried to give (118 g) of 4-(4-(3-(4-chloro-3-(trifluoromethyl)phenyl)ureido)phenoxy)-N-methylpicolinamide (sorafenib base).

Example 23

Synthesis of 1-(4-chloro-3-(trifluoromethyl)phenyl)urea (Compound 4)

Sodium cyanate (1.7 g, 0.02 mol) was dissolved in water (17 ml) at room temperature to obtain a clear solution. This solution was then charged drop wise to the clear solution of 3-trifluoromethyl-4-chloroaniline (5 g, 0.025 mol) in acetic acid (25 ml) at 40° C.-45° C. within 1-2 hours. The reaction mass was agitated for whole day and cooled gradually to room temperature. The obtained solid was filtered washed with water and vacuum dried at 50° C. to afford the desired product (5.8 g), i.e., 1-(4-chloro-3-(trifluoromethyl)phenyl) urea.

Example 24

Synthesis of Sorafenib 1-(4-chloro-3-(trifluoromethyl)phenyl)urea (15 g, 0.0628 mol), 1,8-diazabicyclo[5.4.0]undec-7-ene (11.75 ml, 0.078 mol) and 4-(4-aminophenoxy)-N-methylpicolinamide (15.27 g, 0.0628 mol) were mixed with dimethyl sulfoxide (45 ml) and the reaction mass was then heated to 110-120° C. for 12-18 hours. The reaction mass was cooled to room temperature and quenched in water (250 ml). The quenched mass was extracted repeatedly with ethyl acetate and the combined ethyl acetate layer was then back washed with water. It was dried over sodium sulfate and evaporated under vacuum to obtain solid. The obtained solid was slurried in acetonitrile (150 ml) at ambient temperature and filtered to give 4-(4-(3-(4-chloro-3-(trifluoromethyl)phenyl) ureido) phenoxy)-N-methylpicolinamide (sorafenib base) (17.5 g).

Example 25

Synthesis of 2,2,2-trichloro-N-(4-chloro-3-(trifluoromethyl)phenyl)acetamide. (Compound 3)

The clear solution of 3-trifluoromethyl-4-chloroaniline (45 g, 0.230 mol) and pyridine (37 ml, 0.460 mol) in dichloromethane (450 ml) cooled at 0° C. to −5° C. and a solution of trichloroacetyl chloride (31 ml, 0.2876 mol) in dichloromethane (100 ml) was added drop wise maintaining temperature of the reaction mass below 0° C. The reaction mass was then stirred for 1 hour below 0° C. and quenched with water (250 ml) below 5° C. The organic phase was separated and aqueous layer was re-extracted with dichloromethane. The combined dichloromethane layer was washed with water, dried over sodium sulfate and evaporated under vacuum to obtain (62 g) of the desired product, i.e., 2,2,2-trichloro-N-(4-chloro-3-(trifluoromethyl)phenyl)acetamide.

Example 26

Synthesis of 2,2,2-trichloro-N-(4-chloro-3-(trifluoromethyl)phenyl)acetamide. (Compound 3)

The clear solution of 3-trifluoromethyl-4-chloroaniline (45 g, 0.230 mol) and pyridine (37 ml, 0.460 mol) in dichloromethane (450 ml) cooled at 0° C. to −5° C. and a solution of trichloroacid anhydride (54.85 ml, 0.299 mol) in dichloromethane (100 ml) was added drop wise maintaining temperature of the reaction mass below 0° C. The reaction mass was then stirred for 1 hour below 0° C. and quenched with water (250 ml) below 5° C. The organic phase was separated and aqueous layer was re-extracted with dichloromethane. The combined dichloromethane layer was washed with water, dried over sodium sulfate and evaporated under vacuum to obtain (60 g) of the desired product, i.e., 2,2,2-trichloro-N-(4-chloro-3-(trifluoromethyl)phenyl)acetamide.

Example 27

Synthesis of 2,2,2-trichloro-N-(4-chloro-3-(trifluoromethyl)phenyl)acetamide. (Compound 3)

3-trifluoromethyl-4-chloroaniline (60 g, 0.3067 mol) with ethyl-2,2,2-trichloro acetate (120 ml, 0.6134 mol) were mixed in toluene (600 ml) at room temperature. The mixture was then refluxed for 2-3 hours. The organic solvent was degassed under reduced pressure to obtain oil. This oil was stirred with hexane (1000 ml) to obtain 2,2,2-trichloro-N-(4-chloro-3-(trifluoromethyl)phenyl)acetamide (100 g).

Example 28

Synthesis of Sorafenib 2,2,2-trichloro-N-(4-chloro-3-(trifluoromethyl)phenyl) acetamide (45 g, 0.1319 mol) was refluxed in N,N-dimethyl formamide (100 ml) with 1,8-diazabicyclo[5.4.0]undec-7-ene (24.67 ml, 0.1649 mol) and 4-(4-aminophenoxy)-N-methylpicolinamide (32.07 g, 0.1319 mol) for 24 hours and cooled to room temperature. The reaction mass was quenched in water (1000 ml). The quenched mass was extracted repeatedly with ethyl acetate and the combined ethyl acetate layer was then back washed with water to remove DMF traces. It was dried over sodium sulfate and evaporated under vacuum to obtain solid. The obtained solid was slurried in ethyl acetate (1000 ml) at ambient temperature and filtered to give 4-(4-(3-(4-chloro-3-(trifluoromethyl)phenyl) ureido)phenoxy)-N-methylpicolinamide (sorafenib base) (52 g).

Example 29

Synthesis of 1-(4-chloro-3-(trifluoromethyl)phenyl)-3-hydroxyurea (Compound 9)

Ethyl 4-chloro-3-(trifluoromethyl)phenylcarbamate (10 g, 0.0373 mol) and hydroxyl amine hydrochloride (13 g, 0.1868 mol) were refluxed in acetic acid for 12 hours and the organic layer was evaporated under vacuum to get oil. This oil was mixed with water (100 ml) and the obtained precipitate was stirred at room temperature for 1-2 hours. The obtained solid was filtered and washed thoroughly with water. The wet cake was vacuum dried at 50° C. to afford 1-(4-chloro-3-(trifluoromethyl)phenyl)-3-hydroxyurea (6.8 g) as a white crystalline solid.

Example 30

Synthesis of Sorafenib 1-(4-chloro-3-(trifluoromethyl)phenyl)-3-hydroxyurea (5 g, 0.0196 mol) was suspended in N,N-dimethyl formamide (15 ml) with triethyl amine (8.2 ml, 0.0589 mol) and 4-(4-aminophenoxy)-N-methylpicolinamide (4.7 g, 0.0196 mol). The reaction mass was then heated to 125° C. for 4 days. The reaction mass was concentrated under reduced pressure and the obtained residue was quenched with water (50 ml) at room temperature. The aqueous layer was extracted repeatedly with ethyl acetate and the combined ethyl acetate layer was back washed with water. Degassing of the ethyl acetate gave semisolid which upon agitation in acetonitrile (50 ml) at ambient temperature for 2-3 hours gave desired product. The product was filtered and vacuum dried to obtain 4-(4-(3-(4-chloro-3-(trifluoromethyl)phenyl)ureido)phenoxy)-N-methylpicolinamide (sorafenib base) (2.5 g).

Example 31

Synthesis of Sorafenib Tosylate 4-(4-(3-(4-chloro-3-(trifluoromethyl)phenyl)ureido)phenoxy)-N-methylpicolinamide (sorafenib base) (100 g, 0.2152 mol) was suspended in acetone (1000 ml) at ambient temperature. p-toluene sulfonic acid (50 g, 0.290 mol) was dissolved in acetone (500 ml) and this solution was charged to above reaction mass drop wise in 15 minutes. The obtained precipitate was stirred for 1-2 hours at ambient temperature, filtered and washed with acetone (500 ml). It was vacuum dried for 12 hours at 50° C. to afford 4-(4-(3-(4-chloro-3-(trifluoromethyl)phenyl)ureido)phenoxy)-N-methylpicolinamide tosylate (Sorafenib Tosylate) (130 g).

It will be appreciated that the invention may be modified within the scope of the appended claims.

The invention claimed is:

1. A process for preparing sorafenib or a salt thereof comprising the use of a compound of formula (A)

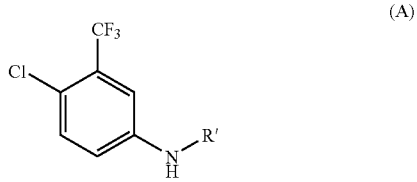

wherein R' is selected from the group consisting of —C(O)OA, —C(O)CX$_3$, —C(O)NH$_2$, —C(O)—NHOH or

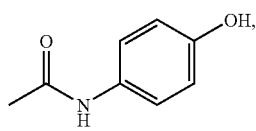

wherein A is alkyl or aryl and X is halogen, wherein compound (A) has formula (2)

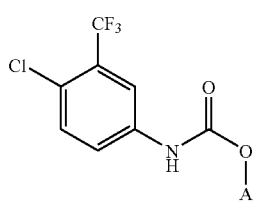

wherein A is alkyl or aryl, the process comprising condensing 4-(4-aminophenoxy)-N-methylpicolinamide or a salt thereof with carbamate derivative (2) to obtain sorafenib, wherein the carbamate derivative (2) is prepared by reacting 3-trifluoromethyl-4-chloroaniline with a haloformate (2a) or a carbonate derivative (2b) in the presence of a base and a solvent at a temperature ranging from −10° C. to 15° C.,

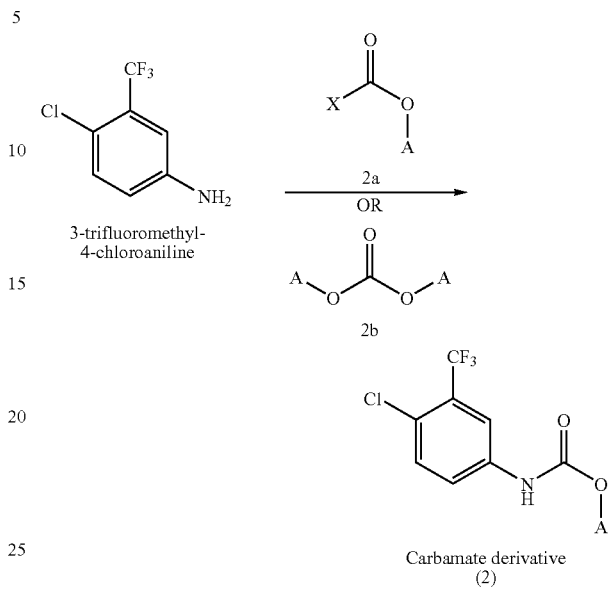

wherein in haloformate (2a), A is alkyl or aryl and X is halogen and in carbonate (2b), A is alkyl, aryl or the two A groups taken together form a 5 to 7 membered ring.

2. The process according to claim 1, wherein compound (A) has formula (3)

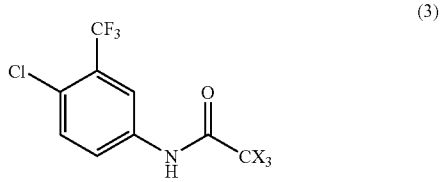

wherein X is halogen, wherein the process comprises condensing 4-(4-aminophenoxy)-N-methylpicolinamide or a salt thereof with anilide derivative (3) in the presence of a base to obtain sorafenib.

3. The process according to claim 2, wherein anilide derivative (3) is prepared by reacting 3-trifluoromethyl-4-chloroaniline with a trihaloalkyl halide, a trihaloalkyl anhydride or a trihaloalkyl ester

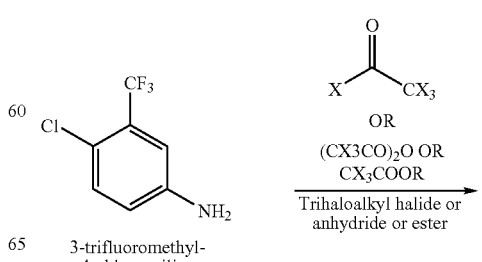

-continued

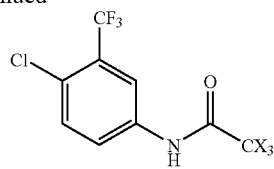

wherein X is halogen and R is alkyl group.

4. The process according to claim 1, wherein compound (A) has formula (4)

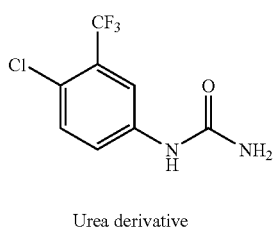

Urea derivative (4)

the process comprising condensing 4-(4-aminophenoxy)-N-methylpicolinamide or a salt thereof with the urea derivative (4) in the presence of a base to obtain sorafenib.

5. The process according to claim 4, wherein urea derivative (4) is prepared by reacting 3-trifluoromethyl-4-chloroaniline with an alkali cyanate in the presence of an acid

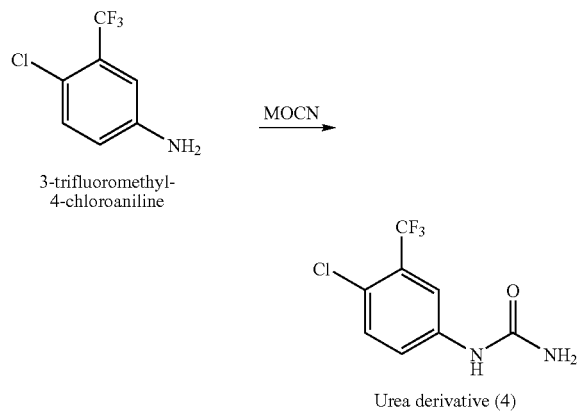

wherein M is an alkali metal.

6. The process according to claim 1, wherein compound (A) has formula (1)

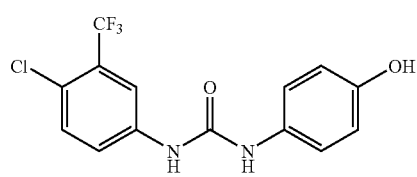

(1)

the process comprising reacting a compound of formula (1) with 4-chloro-N-methyl-2-pyridine carboxamide in the presence of a base to obtain sorafenib

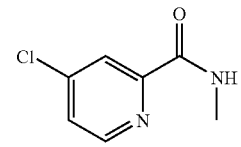

(1)

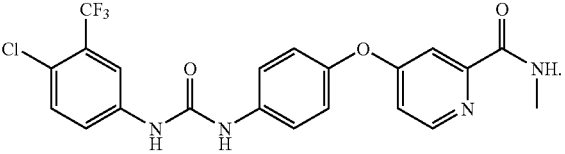

4-chloro-N-methyl-2-pyridine carboxamide

SORAFENIB (I)

7. The process according to claim 6, wherein compound of formula (1) is prepared by reacting carbamate derivative (2) with 4-aminophenol in the presence of a solvent

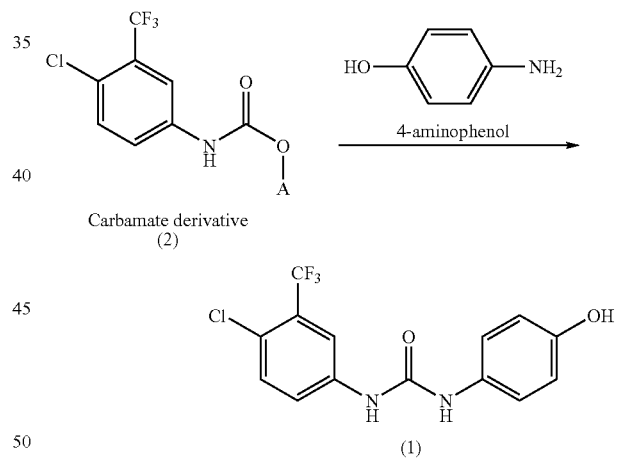

wherein A is alkyl or aryl.

8. The process according to claim 6, wherein compound of formula (1) is prepared by reacting anilide derivative (3) with 4-aminophenol in a solvent to obtain compound (1)

-continued

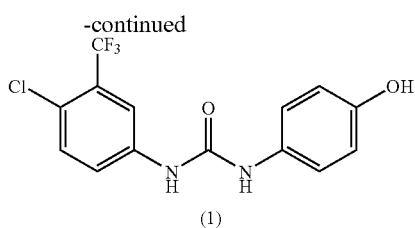

(1)

wherein X is halogen.

9. The process according to claim 6, wherein compound of formula (1) is prepared by reacting urea derivative (4) with 4-aminophenol in a solvent to obtain compound (1)

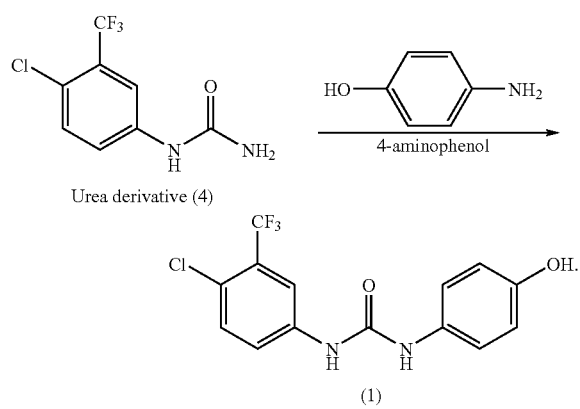

10. The process according to claim 6, wherein compound of formula (1) is prepared by reacting phenoxy urea (5) with 3-trifluoromethyl-4-chloroaniline in a solvent in the presence of a base

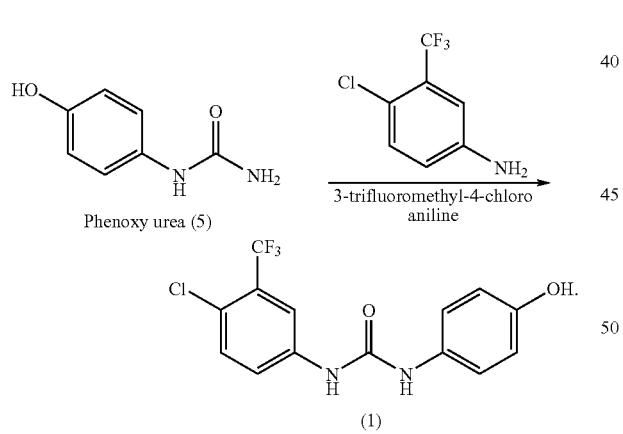

11. The process according to claim 1, wherein compound (A) has formula (9)

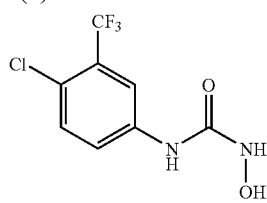

(9)

and the process comprises condensing 4-(4-aminophenoxy)-N-methylpicolinamide or a salt thereof with hydroxy urea derivative (9) to obtain sorafenib.

12. The process according to claim 11, wherein hydroxylurea derivative (9) is prepared by reacting carbamate derivative (2) with a hydroxylamine in a protic solvent

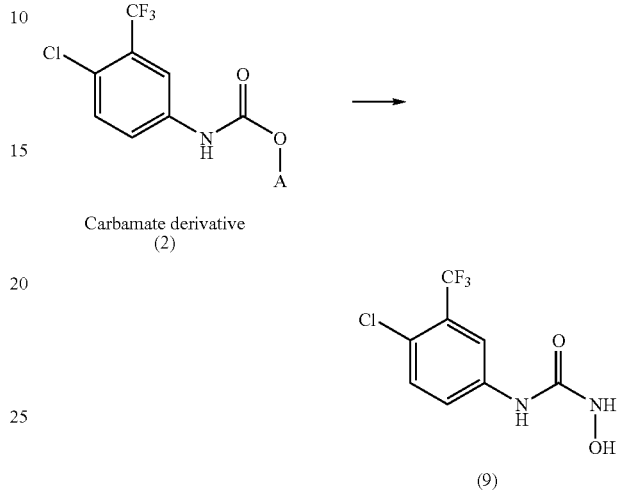

wherein A is alkyl or aryl.

13. The process according to claim 1, wherein sorafenib is converted to sorafenib tosylate.

14. A compound having formula (9)

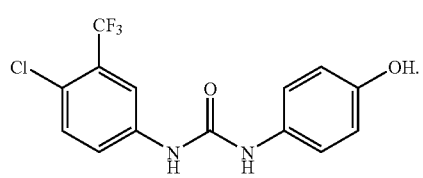

(9)

15. A compound having formula (1)

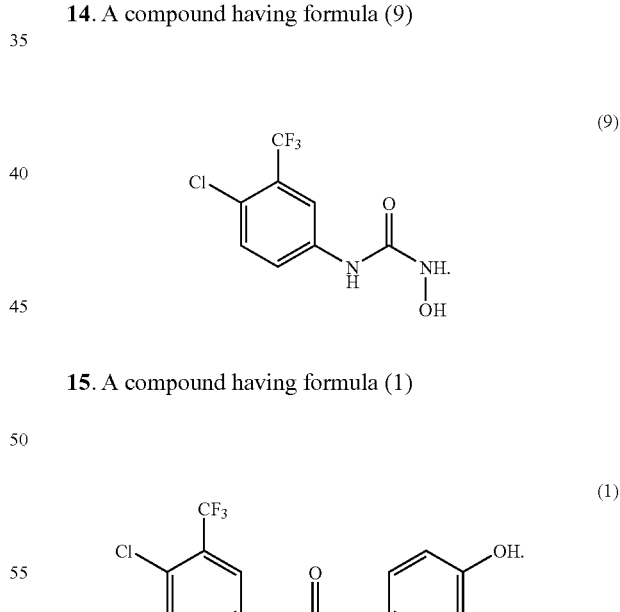

16. The process of claim 1 wherein the carbamate derivative (2) is prepared by reacting 3-trifluoromethyl-4-chloroaniline with a haloformate (2a) or a carbonate derivative (2b) in the presence of a base and a solvent at a temperature ranging from −5° C. to 5° C.

* * * * *

UNITED STATES PATENT AND TRADEMARK OFFICE
CERTIFICATE OF CORRECTION

PATENT NO. : 8,445,687 B2  
APPLICATION NO. : 12/677195  
DATED : May 21, 2013  
INVENTOR(S) : Rao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 75 days.

Signed and Sealed this
Eighth Day of September, 2015

Michelle K. Lee
*Director of the United States Patent and Trademark Office*